United States Patent
Hashino et al.

(10) Patent No.: US 9,381,122 B2
(45) Date of Patent: Jul. 5, 2016

(54) ABSORBENT ARTICLE

(71) Applicant: UNICHARM CORPORATION, Shikokuchuo-shi, Ehime (JP)

(72) Inventors: Akira Hashino, Kanonji (JP); Yuki Noda, Kanonji (JP); Tatsuya Tamura, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/432,026

(22) PCT Filed: Sep. 20, 2013

(86) PCT No.: PCT/JP2013/075574
§ 371 (c)(1),
(2) Date: Mar. 27, 2015

(87) PCT Pub. No.: WO2014/050767
PCT Pub. Date: Apr. 3, 2014

(65) Prior Publication Data
US 2015/0245957 A1    Sep. 3, 2015

(30) Foreign Application Priority Data
Sep. 30, 2012    (JP) .................................. 2012-218984

(51) Int. Cl.
*A61F 13/533*    (2006.01)
*A61F 13/511*    (2006.01)
(Continued)

(52) U.S. Cl.
CPC ........... *A61F 13/51113* (2013.01); *A61F 13/15* (2013.01); *A61F 13/15577* (2013.01);
(Continued)

(58) Field of Classification Search
CPC ........... A61F 13/15203; A61F 13/4704; A61F 13/4756; A61F 13/49001; A61F 13/51104; A61F 13/51108; A61F 13/51113; A61F 13/533; A61F 13/534; A61F 13/53436; A61F 13/536; A61F 13/539; A61F 13/8405; A61F 2013/15284; A61F 2013/15463; A61F 2013/51078; A61F 2013/51083; A61F 2013/51085; A61F 2013/8455; A61F 2013/8461
See application file for complete search history.

(56) References Cited

U.S. PATENT DOCUMENTS 4,559,050 A * 12/1985 Iskra ................. A61F 13/15203
                                                                    604/368
5,069,676 A * 12/1991 Ito ............................ A61F 13/47
                                                                    604/358
(Continued)

FOREIGN PATENT DOCUMENTS

JP        2002-165830 A        6/2002
JP        2002-187228 A        7/2002
(Continued)

OTHER PUBLICATIONS

Atsushi Fujita; "Prediction of Organic Compounds and Organic Conceptual Diagram" Journal of Japanese Chemistry; Oct. 1957, pp. 719-725; vol. 11, No. 10; Kagaku no Ryoiki (Region of Chemistry).
(Continued)

*Primary Examiner* — Lynne Anderson
(74) *Attorney, Agent, or Firm* — Hauptman Ham, LLP

(57) ABSTRACT

In an absorbent article, in which each of pressure-bonded parts has a linear shape extending in the length direction of the absorbent article, the pressure-bonded parts are formed with spacing at regular intervals in a discontinuous manner with respect to the length direction of the absorbent article and are also formed in multiple lines with spacing at regular intervals with respect to the width direction of the absorbent article, depressed parts are formed on a back-sheet-facing surface of an absorbent body that is located beneath the pressure-bonded parts, each of an excretory opening-contacting region in a top sheet and the pressure-bonded parts contains a blood lubricity-imparting agent having a kinematic viscosity of 0.01 to 80 mm²/s at 40° C., a water hold percentage of 0.01 to 4.0 mass % and a weight average molecular weight of less than 1,000, and the amount of the blood lubricity-imparting agent in the pressure-bonded parts is larger than that in the excretory opening-contacting region.

14 Claims, 6 Drawing Sheets

(51) Int. Cl.
*A61F 13/534* (2006.01)
*A61F 13/539* (2006.01)
*A61F 13/475* (2006.01)
*A61L 15/20* (2006.01)
*A61L 15/50* (2006.01)
*A61F 13/84* (2006.01)
*A61F 13/51* (2006.01)
*A61F 13/15* (2006.01)

(52) U.S. Cl.
CPC ....... *A61F13/4756* (2013.01); *A61F 13/51108* (2013.01); *A61F 13/539* (2013.01); *A61F 13/53436* (2013.01); *A61L 15/20* (2013.01); *A61L 15/50* (2013.01); *A61F 2013/15284* (2013.01); *A61F 2013/51078* (2013.01); *A61F 2013/8455* (2013.01)

(56) References Cited

U.S. PATENT DOCUMENTS

| | | | |
|---|---|---|---|
| 5,674,341 A * | 10/1997 | Ng | A61F 13/15699 156/230 |
| 8,211,815 B2 * | 7/2012 | Baker | A61F 13/15707 428/179 |
| 2002/0068150 A1 | 6/2002 | Taneichi et al. | |
| 2003/0050615 A1 | 3/2003 | Sakamoto et al. | |
| 2003/0143376 A1 | 7/2003 | Toyoshima et al. | |
| 2003/0162460 A1 | 8/2003 | Saka et al. | |
| 2005/0147798 A1 | 7/2005 | Toyoshima et al. | |
| 2008/0010795 A1 | 1/2008 | Mizutani et al. | |
| 2008/0200894 A1 | 8/2008 | Gatto et al. | |
| 2009/0221978 A1 | 9/2009 | Gatto et al. | |

FOREIGN PATENT DOCUMENTS

| | | |
|---|---|---|
| JP | 2003-126147 A | 5/2003 |
| JP | 2003-247155 A | 9/2003 |
| JP | 2003-250836 A | 9/2003 |
| JP | 2005-312547 A | 11/2005 |
| JP | 2008-002034 A | 1/2008 |
| JP | 2010-518918 A | 6/2010 |
| JP | 2011-510801 A | 4/2011 |
| WO | 2008/101163 A2 | 8/2008 |
| WO | 2009/102837 A2 | 8/2009 |

OTHER PUBLICATIONS

International Search Report mailed Nov. 26, 2013 in International Patent Application No. PCT/JP2013/075574 filed Sep. 20, 2013.

* cited by examiner (a)

50μm (b)

50μm

ABSORBENT ARTICLE

RELATED APPLICATIONS

The present application is a National Phase of International Application Number PCT/JP2013/075574, filed Sep. 20, 2013, which claims priority to Japanese Application Number 2012-218984, filed Sep. 30, 2012.

TECHNICAL FIELD

The present invention relates to an absorbent article.

BACKGROUND ART

In an absorbent article, such as a sanitary napkin or panty liner, liquid excreta, such as menstrual blood penetrates the liquid-permeable layer, such as the top sheet, and is absorbed and retained by the absorbent body, but due to the high viscosity of menstrual blood it tends to remain in the liquid-permeable layer. When menstrual blood remains in the liquid-permeable layer of an absorbent article, it produces a feeling of stickiness and visual discomfort for the wearer, and it has therefore been a goal to improve the migration of menstrual blood from the liquid-permeable layer to the absorbent body and reduce residual menstrual blood in the liquid-permeable layer.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

Absorbent articles are known in the technical field which are coated with lotion compositions.

For example, PTL 1 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet. Also, PTL 2 discloses an absorbent article wherein a polypropylene glycol material-containing lotion composition is applied on the outer surface of the top sheet (body side surface).

CITATION LIST

Patent Literature

PTL 1 Japanese Unexamined Patent Publication No. 2010-518918
PTL 2 Japanese Unexamined Patent Publication No. 2011-510801

SUMMARY OF INVENTION

Technical Problem

In PTLs 1 to 2, however, the design is not, such as to improve migration of menstrual blood from the top sheet to the absorbent body, and reduce residue of menstrual blood in the top sheet. It is therefore an object of the present invention to provide an absorbent article having improved migration of menstrual blood from the top sheet to the absorbent body, and reduced residue of menstrual blood in the top sheet.

Solution to Problem

In order to solve the problems described above, the invention provides an absorbent article having a liquid-permeable top sheet, a liquid-impermeable back sheet and an absorbent body between the top sheet and the back sheet, wherein the absorbent body is subjected to embossing from the surface facing the back sheet of the absorbent body, a plurality of recesses are formed on the surface facing the back sheet and a dense/sparse structure is formed across the in-plane direction of the absorbent body, while the absorbent body is embossed together with the top sheet from the surface facing the top sheet of the absorbent body, the top sheet and the absorbent body are integrally compressed at the center section in the widthwise direction in the excretory opening contact region on the surface facing the top sheet, forming a plurality of pressure bonded sections where the entirety of the top sheet in the thickness direction introverts into the absorbent body, and the absorbent body and the top sheet are contacted at least in the excretory opening contact region on the surface facing the top sheet, the pressure bonded sections having linear shapes extending in the lengthwise direction of the absorbent article and the pressure bonded sections being formed in a discontinuous manner at prescribed spacings in the lengthwise direction of the absorbent article and being formed in rows at prescribed spacings in the widthwise direction of the absorbent article, the recesses being formed on the surface facing the back sheet of the absorbent body below the pressure bonded sections, the excretory opening contact region of the top sheet and the pressure bonded sections each containing a blood slipping agent with a kinematic viscosity of 0.01 to 80 $mm^2/s$ at 400° C., a water holding percentage of 0.01 to 4.0 mass % and a weight-average molecular weight of less than 1,000, and the amount of blood slipping agent in the pressure bonded sections being greater than the amount of blood slipping agent in the excretory opening contact region.

In the absorbent article of the invention, menstrual blood excreted by the wearer and reaching the excretory opening contact region slips down together with the blood slipping agent present in the excretory opening contact region of the top sheet and the pressure bonded sections, and migrates through the top sheet into the absorbent body. Therefore, the absorbent article of the invention has improved migration of menstrual blood from the top sheet to the absorbent body, and can reduce residue of menstrual blood in the top sheet. This prevents the skin contact surface of the top sheet from having a sticky feel, and maintains a smooth feel. This function and effect of the blood slipping agent is exhibited regardless of changes in menstrual blood discharge during menstruation (that is, whether the amount of discharged menstrual blood is large or small).

Advantageous Effects of Invention

According to the invention there is provided an absorbent article having improved migration of menstrual blood from the top sheet to the absorbent body, which can reduce residue of menstrual blood in the top sheet.

DESCRIPTION OF EMBODIMENTS

<Definitions>

Figure 1:
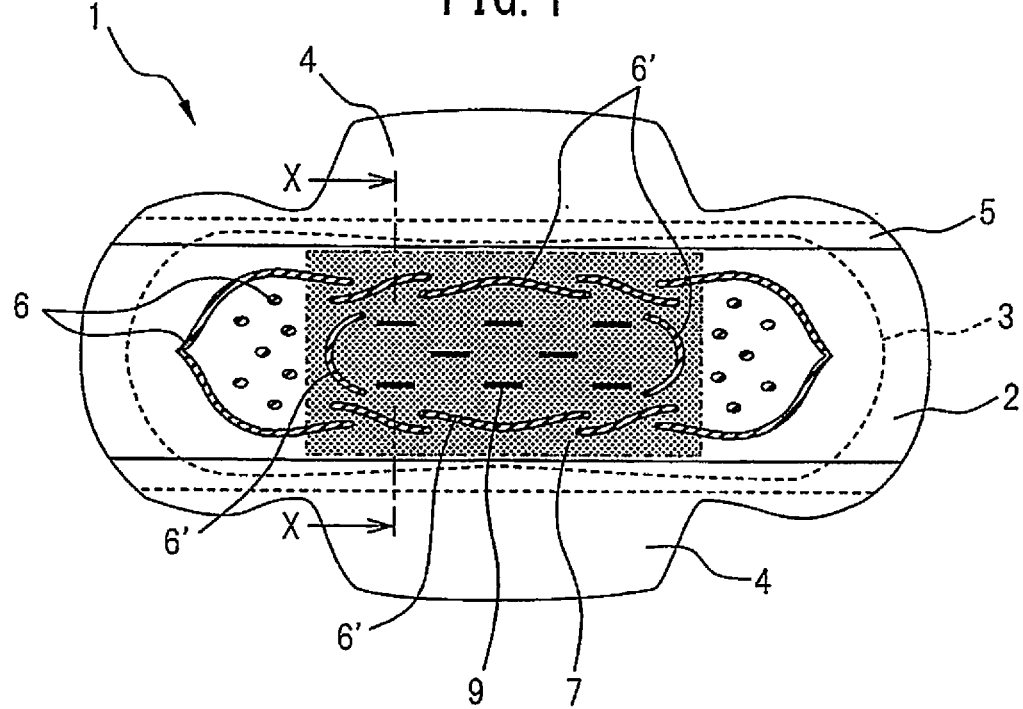
FIG. 1 is a front view of an absorbent article 1 (sanitary napkin), as an embodiment of an absorbent article of the invention.

Some of the terms used throughout the present specification will now be defined.

"Excretory Opening Contact Region"

As used herein, "excretory opening contact region" of the top sheet means the region of the top sheet that contacts with the excretory opening (labia minora, etc.) of the wearer. The excretory opening contact region will have a different location depending on the size of the absorbent article, and for an absorbent article with side flaps, the excretory opening contact region will usually be the inner side of the region defined by embossing disposed in a continuous or discontinuous manner surrounding a lengthwise line running through the widthwise center of the absorbent article, and the intersection with a widthwise line running through the lengthwise centers of both wing sections. Also, in the case of an absorbent article without side flaps, usually the excretory opening contact region is defined by embossing that is disposed continuously or discontinuously surrounding the widthwise center section and the lengthwise center section of the absorbent article.

The absorbent article of the invention may further comprise a second sheet between the top sheet and absorbent body, in addition to the top sheet, in which case the second sheet may have an excretory opening contact region. In this case, the excretory opening contact region of the second sheet is the region overlapping with the excretory opening contact region of the top sheet in the thickness direction of the absorbent article.

"Front" and "Back"

Throughout the present specification, "front" and "back" are in reference to the wearer, and mean the front of the wearer and the back of the wearer, respectively.

"Skin Side Surface" and "Clothing Side Surface"

The "skin side surface", as it relates to the liquid-permeable top sheet and second sheet, means the surface that faces the skin side of the wearer when the article is worn. Similarly, the "clothing side surface" means the surface that faces the clothing side of the wearer when the article is worn. For example, the clothing side surfaces of the top sheet and second sheet are, respectively, the surfaces of the top sheet and second sheet on the back sheet side. Also, the skin side surface of the top sheet has the same definition as "skin contact surface".

"Blood Slipping Agent-Containing Region"

As used herein, the "blood slipping agent-containing region" as it relates to the top sheet means the region of the top sheet containing the blood slipping agent within the excretory opening contact region. The top sheet may have a blood slipping agent-containing region on a portion of the excretory opening contact region, or it may have the blood slipping agent-containing region across the entire excretory opening contact region. Furthermore, the top sheet may also have the blood slipping agent-containing region in the excretory opening non-contact region, exceeding the excretory opening contact region.

Also, throughout the present specification, the second sheet may have a blood slipping agent-containing region. The "blood slipping agent-containing region" as it relates to the second sheet, means the region of the second sheet containing the blood slipping agent within the excretory opening contact region, similar to the top sheet, and the second sheet may have the blood slipping agent-containing region in a portion or the entirety of the excretory opening contact region, while it may also have the blood slipping agent-containing region in the excretory opening non-contact region.

<Absorbent Article>

The absorbent article of the invention will now be explained in detail.

The absorbent article of the invention has a liquid-permeable top sheet, a liquid-impermeable back sheet and an absorbent body between the top sheet and the back sheet, wherein the absorbent body is subjected to embossing from the surface facing the back sheet of the absorbent body, a plurality of recesses are formed on the surface facing the back sheet and a dense/sparse structure is formed across the in-plane direction of the absorbent body, while the absorbent body is embossed together with the top sheet from the surface facing the top sheet of the absorbent body, the top sheet and the absorbent body are integrally compressed at the center section in the widthwise direction in the excretory opening contact region on the surface facing the top sheet, forming a plurality of pressure bonded sections where the entirety of the top sheet in the thickness direction introverts into the absorbent body, and the absorbent body and the top sheet are contacted at least in the excretory opening contact region on the surface facing the top sheet, the pressure bonded sections extending in the lengthwise direction of the absorbent article and the pressure bonded sections being formed in a discontinuous manner at prescribed spacings in the lengthwise direction of the absorbent article and being formed in rows at prescribed spacings in the widthwise direction of the absorbent article, the recesses being formed on the surface facing the back sheet of the absorbent body below the pressure bonded sections, the excretory opening contact region of the top sheet and the pressure bonded sections each containing a blood slipping agent with a kinematic viscosity of 0.01 to 80 $mm^2/s$ at 40° C., a water holding percentage of 0.01 to 4.0 mass % and a weight-average molecular weight of less than 1,000, and the amount of blood slipping agent in the pressure bonded sections being greater than the amount of blood slipping agent in the excretory opening contact region.

In the absorbent article of the invention, because of the blood slipping agent present in the pressure bonded sections and the shapes of the pressure bonded sections extending in the lengthwise direction of the absorbent article, when menstrual blood discharged from the excretory opening contact region attempts to flow in the widthwise direction of the absorbent article, the menstrual blood does not stop at the pressure bonded section but is repelled, and the menstrual blood is guided in the lengthwise direction of the absorbent article, thus allowing menstrual blood to be absorbed while efficiently using the absorbent body. Also, although menstrual blood tends to pool at the pressure bonded sections, the presence of the blood slipping agent allows the menstrual blood to migrate into the absorbent body without stopping at the top sheet.

The pressure bonded sections of the absorbent article of the invention contain the blood slipping agent at a basis weight of preferably 1 to 30 g/m$^2$, more preferably 2 to 20 g/m$^2$ and even more preferably 3 to 10 g/m$^2$. The excretory opening contact region of the top sheet contains the blood slipping agent at a basis weight of preferably 0.01 to 20 g/m$^2$ and more preferably 0.1 to 10 g/m$^2$. However, the amount of blood slipping agent in the pressure bonded sections must be greater than the amount of blood slipping agent in the excretory opening contact region.

The pressure bonded sections of the absorbent article of the invention are not particularly restricted so long as they extend in the lengthwise direction of the absorbent article, and for example, they may be straight linear, dotted, dotted linear, creased linear, curved linear, polygonal, circular, rectangular, punched circular, rectangular or polygonal recesses connected in an essentially linear fashion as recess groups. When the pressure bonded sections are a plurality of dotted recesses connected in an essentially linear fashion as recess groups, each of the dotted recesses preferably have areas of 0.5 to 2.0 mm$^2$ and especially 1 to 1.0 mm$^2$. The distances between the dotted recesses are preferably no greater than 5 mm and especially no greater than 3 mm, from the viewpoint of effectively guiding fluid in the direction in which the pressure bonded sections extend.

The shapes of the recesses formed on the surface facing the back sheet of the absorbent body of the absorbent article of the invention may be any desired shapes, and for example, they may be polygonal, dotted, linear, ellipsoid, punched circular, wavy linear or the like. They may also be a pattern of these shapes in any desired combination of two or more.

In the absorbent article of the invention, the embossed sections are provided surrounding the excretory opening contact region, the embossed sections preferably containing a blood slipping agent. If embossed sections are present around the excretory opening contact region and the embossed sections also contain a blood slipping agent, then it will be possible to cause menstrual blood to diffuse along the embossed sections around the excretory opening contact region while pushing back menstrual blood that has flowed over the pressure bonded sections in the widthwise direction of the absorbent article, thus exhibiting a greater effect of preventing side leakage.

In the absorbent article of the invention, the top sheet has a plurality of projections on the skin side surface of the top sheet, and the clothing side surface of the top sheet is preferably flatter than the skin side surface of the top sheet.

In the absorbent article of the invention, the top sheet preferably has a gradually densifying structure from the skin side surface of the top sheet toward the clothing side surface of the top sheet.

In the absorbent article of the invention, the top sheet also preferably has gradually increasing hydrophilicity from the skin side surface of the top sheet toward the clothing side surface of the top sheet.

The top sheet in the absorbent article of the invention also preferably has stretchability.

In the absorbent article of the invention, the total ratio of the area of the recesses with respect to the surface facing the back sheet of the absorbent body is preferably higher than the total ratio of the area of the pressure bonded sections with respect to the surface facing the top sheet.

In the absorbent article of the invention, the recesses formed on the surface facing the back sheet of the absorbent body are preferably dotted recesses.

In both the lengthwise direction and/or the widthwise direction of the absorbent article of the invention, preferably the pitch between the pressure bonded sections formed on the surface facing the top sheet is greater than the pitch between the recesses formed on the surface facing the back sheet of the absorbent body.

In the absorbent article of the invention, preferably the total ratio of the area of the recesses with respect to the surface facing the back sheet of the absorbent body is between 1 and 50%, the pitch between the recesses in the lengthwise direction is 3 to 10 mm, and the pitch in the widthwise direction is 3 to 10 mm.

In the absorbent article of the invention, preferably the total ratio of the area of the pressure bonded sections with respect to the surface facing the top sheet of the absorbent body is between 0.01 and 2.0%, the area of each of the pressure bonded sections is 1 to 20 mm$^2$, the pitch between the pressure bonded sections in the lengthwise direction is 5 to 50 mm, and the pitch in the widthwise direction is 5 to 30 mm.

In the absorbent article of the invention, the IOB of the blood slipping agent is preferably an IOB of 0.00 to 0.60.

In the absorbent article of the invention, preferably the blood slipping agent is selected from the group consisting of following items (i) to (iii), and any combination thereof:
 (i) a hydrocarbon;
 (ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and
 (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;
 with the proviso that when two or more oxy groups are inserted in the compound of (ii) or (iii), the oxy groups are not adjacent.

Also in the absorbent article of the invention, preferably the blood slipping agent is selected from the group consisting of following items (i') to (iii'), and any combination thereof:
 (i') a hydrocarbon;
 (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
 (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;
 with the proviso that when two or more same or different bonds are inserted in the compound of (ii') or (iii'), the bonds are not adjacent.

Furthermore, in the absorbent article of the invention, preferably the blood slipping agent is selected from the group consisting of following items (A) to (F), as well as any combination thereof:
 (A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

Yet further in the absorbent article of the invention, preferably the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

(Blood Slipping Agent)

The blood slipping agent contained in the absorbent article of the invention will now be described. The blood slipping agent has a kinematic viscosity of about 0.01 to about 80 mm$^2$/s at 40° C., a water holding percentage of about 0.05 to about 4.0 mass %, and a weight-average molecular weight of less than about 1,000.

The 40° C. kinematic viscosity of the blood slipping agent may be appropriately adjusted in the range of about 0 to about 80 mm$^2$/s, but it is preferably about 1 to about 70 mm$^2$/s, more preferably about 3 to about 60 mm$^2$/s, even more preferably about 5 to about 50 mm$^2$/s and yet more preferably about 7 to about 45 mm$^2$/s. As used herein, the "40° C. kinematic viscosity" may be referred to simply as "kinematic viscosity".

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm$^2$/s at 40° C., the melting point of the blood slipping agent is preferably no higher than 45° C. This is because the kinematic viscosity will tend to be higher if the blood slipping agent contains crystals at 40° C.

The significance of the kinematic viscosity of the blood slipping agent will be explained below, but a kinematic viscosity exceeding about 80 mm$^2$/s will tend to result in high viscosity of the blood slipping agent, such that it will not as easily slip down from the projections to the recesses together with menstrual blood that has reached the skin contact surface of the top sheet, and subsequently migrate into the absorbent body.

The kinematic viscosity can be measured according to JIS K 2283:2000, "5. Kinematic Viscosity Test Method", using a Cannon-Fenske reverse-flow viscometer, at a testing temperature of 40° C.

The water holding percentage of the blood slipping agent may be appropriately adjusted in the range of about 0.01 to about 4.0 mass %, but it is preferably about 0.02 to about 3.5 mass %, more preferably about 0.03 to about 3.0 mass %, even more preferably about 0.04 to about 2.5 mass % and yet more preferably about 0.05 to about 2.0 mass %.

As used herein, "water holding percentage" means the percentage (mass) of water that can be held by a substance, and it may be measured in the following manner.

(1) A 20 mL test tube, a rubber stopper, the substance to be measured and deionized water are allowed to stand for a day and a night in a thermostatic chamber at 40° C.

(2) Into the test tube in the thermostatic chamber there are charged 5.0 g of the substance to be measured and 5.0 g of deionized water.

(3) The mouth of the test tube is closed with the rubber stopper in the thermostatic chamber, and the test tube is rotated once and allowed to stand for 5 minutes.

(4) A 3.0 g portion of the layer of the substance to be measured (usually the upper layer) is sampled into a glass dish with a diameter of 90 mm and a mass of $W_0$ (g), in the thermostatic chamber.

(5) The dish is heated at 105° C. for 3 hours in an oven to evaporate off the moisture, and the mass $W_1$ (g) of each dish is measured.

(6) The water holding percentage is calculated by the following formula.

Water holding percentage (mass %)=100×[$W_0$ (g)–$W_1$ (g)]/3.0 (g)

The measurement is conducted three times, and the average value is recorded.

The significance of the water holding percentage of the blood slipping agent will be explained below, but a low water holding percentage will tend to lower the affinity between the blood slipping agent and menstrual blood, thus impeding its migration into the absorbent body together with menstrual blood that has reached the skin contact surface of the top sheet. If the water holding percentage is high, on the other hand, the affinity between menstrual blood and the blood modifying agent will become very high, similar to a surfactant, and absorbed menstrual blood will tend to remain on the skin contact surface of the top sheet, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e with a higher inorganic value or with a lower organic value. This is also because the blood slipping agent has greater hydrophilicity.

The significance of the kinematic viscosity and water holding percentage of the blood slipping agent will now be explained.

Menstrual blood excreted by the wearer and reaching the excretory opening contact region contacts the blood slipping agent in the projections and slips down together with it into the recesses, passing through the top sheet and migrating into the absorbent body.

More specifically, since the blood slipping agent with a kinematic viscosity of about 0.01 to about 80 mm$^2$/s at 40° C. has very low viscosity near the body temperature of the wearer and has a constant affinity with the menstrual blood, it slips down from the projections to the recesses together with the menstrual blood, and utilizing the energy during sliding, the menstrual blood is able to pass through the recesses of the top sheet to rapidly migrate into the absorbent body. Also, since the blood slipping agent present in the projections has a water holding percentage of about 0.01 to about 4.0 mass %, presumably it has no affinity with the hydrophilic component (blood plasma, etc.) in the menstrual blood, and therefore the menstrual blood does not easily remain on the top sheet.

When the menstrual blood discharged by the wearer is a large amount of menstrual blood, the menstrual blood easily migrates into the absorbent body, even when the kinetic energy of the menstrual blood itself is high and the kinematic viscosity of the blood slipping agent is relatively high so that it does not easily slip down together with the menstrual blood, or when the water holding percentage value is relatively high so that affinity with the hydrophilic components of the menstrual blood is high, or when the weight-average molecular weight value is relatively high so that it does not easily slip down together with the menstrual blood, or when the skin contact surface of the top sheet does not have an irregular structure.

When the menstrual blood discharge by the wearer is a small amount of menstrual blood, on the other hand, the kinetic energy of the menstrual blood is low, and menstrual blood that has reached the skin contact surface of the top sheet tends to easily pool in such cases. Consequently, the blood slipping agent slips down from the projections into the recesses together with the menstrual blood, and the menstrual blood is drawn into the top sheet and then drawn into the absorbent body, so that the menstrual blood can rapidly migrate into the absorbent body.

The blood slipping agent has a weight-average molecular weight of less than about 1,000, and preferably a weight-average molecular weight of less than about 900. This is because if the weight-average molecular weight is about 1,000 or higher, tack may be produced in the blood slipping agent itself, tending to create a feeling of discomfort for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 ... ), it refers to $M_w$ determined by the following formula.

$$M_w = \Sigma N_i M_i^2 / \Sigma N_i M_i$$

The weight-average molecular weights used throughout the present specification are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

The blood slipping agent may have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=Inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso branching | 0 | −10 |
| tert branching | 0 | −20 |
| Light metal (salts) | ≥500 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of no higher than 45° C., and more preferably it has a melting point of no higher than 40° C. If the blood slipping agent has a melting point of no higher than 45° C., the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of no higher than about 45° C., it may be either liquid or solid at room temperature (about 25° C.), or in other words, the melting point may be either about 25° C. or higher or below about 25° C., and for example, it may have a melting point of about −5° C. or about −20° C.

The blood slipping agent does not have a lower limit for its melting point, but its vapor pressure is preferably low. The vapor pressure of the blood slipping agent is preferably between about 0 and about 200 Pa, more preferably between about 0 and about 100 Pa, more preferably between about 0 and about 10 Pa, even more preferably between about 0 and about 1 Pa and yet more preferably between about 0.0 and about 0.1 Pa, at 25° C. (1 atmosphere).

Considering that the absorbent article of the invention is to be used in contact with the human body, the vapor pressure is preferably between about 0 and about 700 Pa, more preferably between about 0 and about 100 Pa, more preferably between about 0 and about 10 Pa, even more preferably between about 0 and about 1 Pa and yet more preferably between about 0.0 and about 0.1 Pa, at 40° C. (1 atmosphere). If the vapor pressure of the blood slipping agent is high, gasification may occur during storage and the amount may be reduced, often creating problems, such as odor during wear.

The melting point of the blood slipping agent may be selected depending on the weather or duration of wear. For example, in regions with a mean atmospheric temperature of no higher than about 10° C., using a blood slipping agent with a melting point of no higher than about 10° C. may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of no higher than about 45° C. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

The blood slipping agent is preferably selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen on the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as "alkane"), an olefin-based hydrocarbon (containing one double bond, also referred to as "alkene"), an acetylene-based hydrocarbon (containing one triple bond, also referred to as "alkyne"), or a hydrocarbon or cyclic hydrocarbon comprising two or more bonds selected from the group consisting of double bonds or triple bonds, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include straight-chain hydrocarbons and branched-chain hydrocarbons.

When two or more oxy groups (—O—) are inserted in the compounds of (ii) and (iii) above, the oxy groups (—O—) are not adjacent. Thus, compounds (ii) and (iii) do not include compounds with continuous oxy groups (i.e. peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

The blood slipping agent is more preferably selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more identical or different bonds are inserted in a compound of (ii') or (iii'), that is, when 2 or more identical or different bonds selected from among carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent more preferably has no more than about 1.8 carbonyl bonds (—CO—), no more than two ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

The blood slipping agent is even more preferably selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or ester or ether thereof; and (F) a chain hydrocarbon.

The blood slipping agent according to (A) to (F) will now be explained in detail.

[(A) Ester of (A1) a Compound Having a Chain Hydrocarbon Moiety and 2-4 Hydroxyl Groups Substituting for Hydrogens on the Chain Hydrocarbon Moiety, and (A2) a Compound Having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples for the (A1) compound having a chain hydrocarbon moiety and 2-4 hydroxyl groups substituting at hydrogens of the chain hydrocarbon moiety (hereunder also referred to as "compound (A1)") include chain hydrocarbon tetraols, such as alkanetetraols including pentaerythritol, chain hydrocarbon triols, such as alkanetriols including glycerin, and chain hydrocarbon diols, such as alkanediols including glycols.

Compounds for the (A2) compound having a chain hydrocarbon moiety and one carboxyl group substituting at a hydrogen of the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of esters of a chain hydrocarbon tetraol and at least one fatty acid include tetraesters of pentaerythritols and fatty acids, represented by the following formula (1):

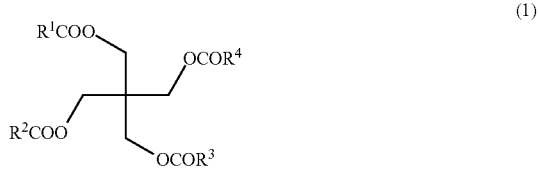

triesters of pentaerythritol and fatty acids, represented by the following formula (2):

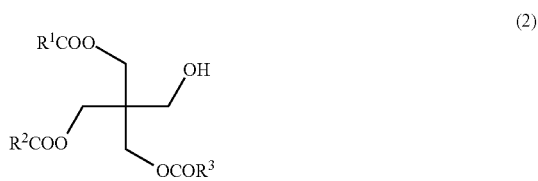

diesters of pentaerythritol and fatty acids, represented by the following formula (3):

and monoesters of pentaerythritol and fatty acids, represented by the following formula (4).

wherein, $R^1$ to $R^4$ each represent a chain hydrocarbon.

The fatty acids composing the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of $R^1C$, $R^2C$, $R^3C$ or $R^4C$, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing that have not been mentioned.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), as well as partial hydrogen adducts of the foregoing.

Considering the potential for degradation by oxidation and the like, the ester of pentaerythritol and a fatty acid is preferably an ester of pentaerythritol and a fatty acid derived from a saturated fatty acid, or in other words, an ester of pentaerythritol and a saturated fatty acid.

Also, in order to lower the water holding percentage value, the ester of pentaerythritol and a fatty acid is preferably a diester, triester or tetraester, more preferably a triester or tetraester, and most preferably a tetraester.

From the viewpoint of the IOB being from about 0.00 to about 0.60, for a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

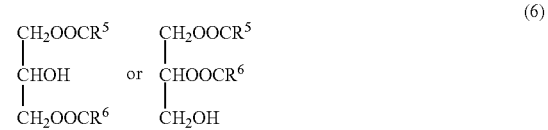

and monoesters of glycerin and fatty acids, represented by the following formula (7):

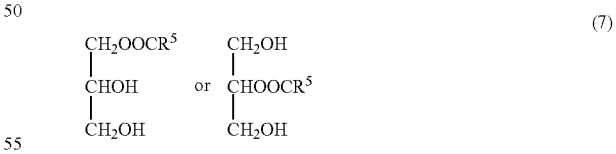

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of chain hydrocarbon tetraol and at least one fatty acid", namely saturated fatty acids and unsaturated fatty acids, and in consideration of the potential for degradation by oxidation and the like, the ester is preferably a glycerin and fatty acid ester derived from a saturated fatty acid, or in other words, an ester of glycerin and a saturated fatty acid.

Also, from the viewpoint of lowering the water holding percentage value, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

Considered from the viewpoint of obtaining a melting point of no higher than about 45° C., the triester of glycerin and a fatty acid preferably has a total number of carbon atoms in the fatty acid composing the triester of glycerin and a fatty acid, i.e. a total number of carbons in the $R^5C$, $R^6C$ and $R^7C$ portions in formula (5), of no greater than about 40.

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of esters of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of esters of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2 to 6, and $R^8$ and $R^9$ each represent a chain hydrocarbon,
and monoesters of $C_2$-$C_6$ glycols and fatty acids, represented by the following formula (9):

$$R^8COOC_kH_{2k}OH \qquad (9)$$

wherein k represents an integer of 2 to 6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage value, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage value, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

The (B1) compound having a chain hydrocarbon moiety and 2-4 hydroxyl groups substituting at hydrogens of the chain hydrocarbon moiety (hereunder also referred to as "compound (B1)"), may be pentaerythritol, glycerin or glycol, for example, mentioned as compound (A1) for "compound (A)".

The (B2) compound having a chain hydrocarbon moiety and one hydroxyl group substituting at a hydrogen of the chain hydrocarbon moiety (hereunder also referred to as "compound (B2)") may be, for example, a compound in which one hydrogen of the hydrocarbon is substituted with one hydroxyl group (—OH), such as an aliphatic monohydric alcohol, which may be a saturated aliphatic monohydric alcohol or an unsaturated aliphatic monohydric alcohol.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein one C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($b_1$) ethers of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) ethers of a chain hydrocarbon triol and at least one aliphatic monohydric alcohol, such as monoethers, diethers and triethers, preferably diethers and triethers and more preferably triethers, and ($b_3$) ethers of a chain hydrocarbon diol and at least one aliphatic monohydric alcohol, such as monoethers and diethers, and preferably diethers.

Examples of ethers of a chain hydrocarbon tetraol and at least one aliphatic monohydric alcohol include tetraethers, triethers, diethers and monoethers of pentaerythritol and aliphatic monohydric alcohols, represented by the following formulas (10) to (13):

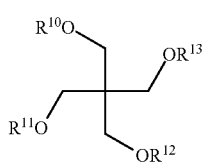
(10)

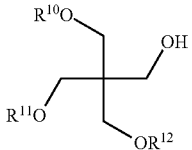
(11)

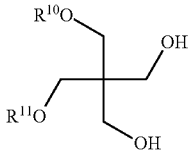
(12)

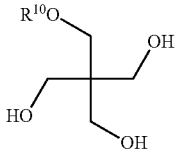
(13)

wherein $R^{10}$-$R^{13}$ each represent a chain hydrocarbon.

Examples of ethers of chain hydrocarbon triol and at least one aliphatic monohydric alcohol include triethers, diethers and monoethers of glycerin and aliphatic monohydric alcohols, represented by the following formulas (14) to (16):

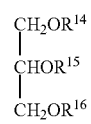
(14)

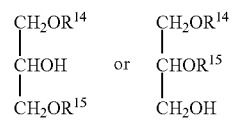
(15)

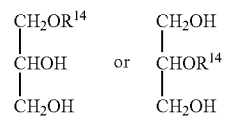
(16)

wherein $R^{14}$-$R^{16}$ each represent a chain hydrocarbon.

Ethers of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2 to 6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2 to 6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) can be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples for the (C1) carboxylic acid, hydroxy acid, alkoxy acid or oxoacid including a chain hydrocarbon moiety and 2-4 carboxyl groups substituting hydrogens of the chain hydrocarbon moiety (hereunder also referred to as "compound (C1)") include chain hydrocarbon carboxylic acids with 2-4 carboxyl groups, for example, chain hydrocarbon dicarboxylic acids, which include alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, which include alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, which include alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Also, compound (C1) includes chain hydrocarbon hydroxy acids with 2-4 carboxyl groups, for example, chain hydrocarbon alkoxy acids with 2-4 carboxyl groups, such as malic acid, tartaric acid, citric acid and isocitric acid, and O-acetylcitric acid or chain hydrocarbon oxoacids with 2-4 carboxyl groups.

The (C2) compound with a chain hydrocarbon moiety and one hydroxyl group substituting at a hydrogen of the chain hydrocarbon moiety may be any of those mentioned for "compound (B)", such as an aliphatic monohydric alcohol.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of fatty acids and aliphatic monohydric alcohols include compounds having the following formula (21):

$$R^{23}COOR^{24} \qquad (21)$$

wherein $R^{23}$ and $R^{24}$ each represent a chain hydrocarbon.

Examples of fatty acids composing esters (corresponding to $R^{23}COOH$ in formula (21)) include the fatty acids mentioned for the "($a_1$) esters of chain hydrocarbon tetraols and fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

The dialkyl carbonate may be a commercially available product, or it may be synthesized by reaction between phosgene and an alcohol, reaction between formic chloride ester and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately −50° C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

The polyoxy $C_3$-$C_6$ alkylene glycol is i) a homopolymer having one backbone selected from the group consisting of oxy $C_3$-$C_6$ alkylene backbones, i.e. oxyethylene backbone, oxypropylene backbone, oxybutylene backbone, oxypentylene backbone and oxyhexylene backbone, and having hydroxy groups at both ends, ii) a block copolymer having a backbone of two or more selected from among the aforementioned group and having hydroxy groups at both ends, or iii) a random copolymer having a backbone of two or more selected from among the aforementioned group and having hydroxy groups at both ends.

A polyoxy $C_3$-$C_6$ alkylene glycol is represented by the following formula (23):

$$HO-(C_mH_{2m}O)_n-H \qquad (23)$$

wherein m is an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥about 7 (when n=7, the IOB is 0.57).

Examples of commercial products of poly $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

The ester of a polyoxy $C_3$-$C_6$ alkylene glycol and at least one fatty acid may be one wherein one or both of the OH ends of a polyoxy $C_3$-$C_6$ alkylene glycol mentioned above under "($e_1$) Polyoxy $C_3$-$C_6$ alkylene glycol" are esterified by a fatty acid, i.e. a monoester or a diester.

Examples of fatty acids to be esterified in the ester of a polyoxy $C_3$-$C_6$ alkylene glycol and at least one fatty acid include the fatty acids mentioned above under "($a_1$) Ester of chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

The ether of a polyoxy $C_3$-$C_6$ alkylene glycol and at least one aliphatic monohydric alcohol may be one wherein one or both of the OH ends of a polyoxy $C_3$-$C_6$ alkylene glycol mentioned above under "($e_1$) Polyoxy $C_3$-$C_6$ alkylene glycol" are etherified by an aliphatic monohydric alcohol, i.e. a monoether or diether.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of no higher than about 45° C. have up to about 22 carbon atoms, and at a vapor pressure of 1 atmosphere and no greater than about 0.01 Pa at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C. Examples of commercially available hydrocarbon products include PARLEAM 6 (NOF Corp.).

In an absorbent article according to one embodiment of the invention, the top sheet contains only a blood slipping agent in the excretory opening contact region. In an absorbent article according to another embodiment of the invention, the top sheet contains, in the excretory opening contact region, a blood slipping agent-containing composition including the aforementioned blood slipping agent and at least one other component. Such a blood slipping agent-containing composition will now be described.

[Blood Slipping Agent-Containing Composition]

The blood slipping agent-containing composition contains a blood slipping agent and at least one other component. The other component is not particularly restricted so long as it does not inhibit the effect of the invention, and it may be any one commonly employed in absorbent articles of the art, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including vitamin $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins.

The derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, salvia extract, linden extract, common lime extract, white birch extract, common horsetail extract, sage extract, salvia extract, walnut (*J. regia* L. var. *orientalis*) extract, hibiscus extract, loquat leaf extract, Miquel's linden extract, hop extract, common horse-chestnut extract and coix seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts. Examples of anti-inflammatory components include naturally-derived anti-inflammatory drugs, such as peony, golden grass, otogiriso, chamomile, licorice, peach leaf, Japanese mugwort and perilla extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. These ranges are from the viewpoint of the effect of the invention.

The blood slipping agent-containing composition preferably contains a surfactant in no greater than the amount from hydrophilicizing treatment of the top sheet or second sheet. More specifically, the blood slipping agent-containing composition contains a surfactant in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$.

This is because when the amount of surfactant is increased, menstrual blood will tend to be retained in the top sheet. The surfactant, incidentally, has no water holding percentage. This is because there is no layer of the substance to be measured due to its mixture with water.

The blood slipping agent-containing composition contains water in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$.

Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 mm$^2$/s, more preferably a kinematic viscosity of about 1 to about 70 mm$^2$/s, even more preferably a kinematic viscosity of about 3 to about 60 mm$^2$/s, yet more preferably a kinematic viscosity of about 5 to about 50 mm$^2$/s, and even yet more preferably a kinematic viscosity of about 7 to about 45 mm$^2$/s.

If the kinematic viscosity of the blood slipping agent-containing composition exceeds 80 mm$^2$/s, the viscosity will increase, and the blood slipping agent composition may not slip down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1,000, and more preferably a weight-average molecular weight of less than about 900. This is because, if the weight-average molecular weight is about 1,000 or higher, tack may result in the blood slipping agent-containing composition itself, tending to create a feeling of unpleasantness for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from slipping down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

There are no particular restrictions on the type and usage of the absorbent article of the invention. For example, absorbent articles include sanitary products and sanitary articles, such as sanitary napkins and panty liners, which may be for humans or animals other than humans, such as pets. The liquid to be absorbed by the absorbent article is not particularly restricted, but will mainly be liquid excreta, such as menstrual blood. With an absorbent article of the invention, there is no need for components, such as emollients and immobilizing agents, unlike in an absorbent article containing a known skin care composition, lotion composition or the like.

Embodiments of the absorbent article of the invention will now be described in further detail with reference to the accompanying drawings, using a sanitary napkin as an example of an absorbent article of the invention. Incidentally, the absorbent article of the invention is not limited to the embodiment of the invention shown in the drawings, such as is within the scope of the object and gist of the invention.

FIG. 1 is a front view of an absorbent article 1, and more specifically a front view of a sanitary napkin, according to an embodiment of the invention. FIG. 1 is as observed from the skin side surface of the top sheet 2. The absorbent article 1 shown in FIG. 1 has a liquid-permeable top sheet 2, a liquid-impermeable back sheet (not shown), and an absorbent body 3 between the top sheet 2 and the back sheet. In the absorbent article 1 shown in FIG. 1, a pair of side flaps 4 are provided on both edges in the lengthwise direction of the absorbent article 1, to anchor the absorbent article 1 to the clothing of the wearer, such as shorts.

In the absorbent article 1 shown in FIG. 1, the left side is the front. In the absorbent article 1 shown in FIG. 1, the excretory opening contact region is the region defined by four embossings 6' within the blood slipping agent-containing region 7, and all of the excretory opening contact regions of the top sheet 2 have a blood slipping agent-containing region 7.

Also, the absorbent article 1 shown in FIG. 1 has a side sheet 5 and a plurality of embossings 6, but the absorbent article according to another embodiment of the invention may lack either or both a side sheet and/or embossing. In the absorbent article shown in FIG. 1, the top sheet 2 is formed of a nonwoven fabric, but in an absorbent article according to another embodiment of the invention, the top sheet may be formed of a woven fabric or porous film.

In the absorbent article 1 shown in FIG. 1, at least the excretory opening contact region of the top sheet 2 has a blood slipping agent-containing region 7 containing a blood slipping agent having a kinematic viscosity of 0.01 to 80 mm$^2$/s at 40° C., a water holding percentage of 0.01 to 4.0 mass % and a weight-average molecular weight of less than 1,000.

In the absorbent article 1 shown in FIG. 1, pressure bonded sections 9 are formed at a plurality of locations at the widthwise center section A in the region facing the excretory opening on the skin contact surface side. The pressure bonded sections 9 have straight linear shapes. The pressure bonded sections 9 are formed so as to extend in the lengthwise direction of the absorbent article 1. The pressure bonded sections 9 are formed in a discontinuous manner with prescribed spacings in the lengthwise direction of the absorbent article 1. They are also formed in a plurality of rows with prescribed spacings in the widthwise direction of the absorbent article 1.

Figure 2:
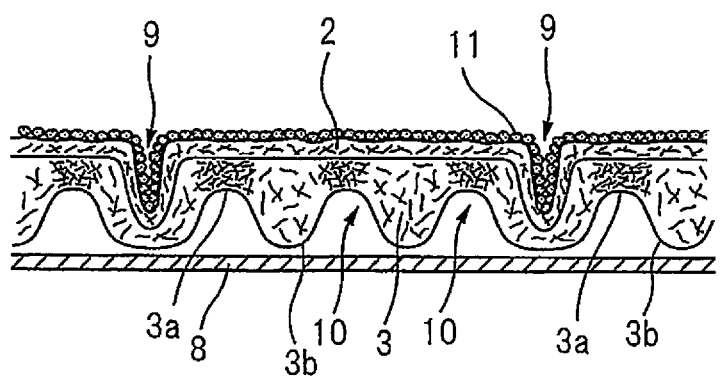
FIG. 2 is a cross-sectional view of the blood slipping agent-containing region 7 of the absorbent article 1 shown in FIG. 1, along cross-section X-X.

FIG. 2 is a cross-sectional view of the blood slipping agent-containing region 7 of the absorbent article 1 shown in FIG. 1, along cross-section X-X. As shown in FIG. 2, the absorbent article 1 has pressure bonded sections 9 formed by integrally compressing the top sheet 2 and the absorbent body 3, with a plurality of dotted recesses 10 formed on the surface facing the back sheet of the absorbent body 3, the excretory opening contact region of the top sheet 2 and the pressure bonded sections 9 each containing a blood slipping agent 11, the amount of blood slipping agent 11 in the pressure bonded sections 9 being greater than the amount of blood slipping agent in the excretory opening contact region.

The recesses 10 are preferably provided at least at the excretory opening-facing region on the surface facing the back sheet of the absorbent body 3, and are formed on the absorbent article 1 across the entire surface facing the back sheet. The recesses 10 are formed by embossing of the absorbent body 3 from the surface facing the back sheet of the absorbent body 3. However, the absorbent body 3 is not embossed from the surface facing the top sheet, except for the excretory opening-facing region described below. As a result, the surface facing the back sheet of the absorbent body 3 becomes an irregular surface, while the surface facing the top sheet is essentially a flat surface. In some cases, however, the surface facing the top sheet is slightly indented at the locations corresponding to the recesses 10, depending on the embossing conditions during formation of the recesses 10.

The embossing for formation of the recesses 10 is carried out only on the absorbent body 3. That is, the recesses 10 are not formed by embossing of the absorbent body 3 together with the top sheet 2 or back sheet 8.

Also, by embossing the absorbent body 3 from the surface facing the back sheet, a dense/sparse structure is formed in the absorbent body 3 across the entire in-plane direction. Specifically a dense/sparse structure is formed comprising dense sections 3a that are compressed and sparse sections 3b that are in a non-compressed state. The dense sections 3a are located on the bottom sections of the recesses 10.

By forming a dense/sparse structure in the absorbent body 3, it is possible to impart two functions to the absorbent body 3. The first function is a function of increasing diffusibility of fluids due to the presence of the dense sections 3a. At the dense sections 3a, capillary force is strongly active causing rapid diffusion of fluid in the planar direction of the absorbent body 3. The second function is a function of increasing permeability of fluids due to the presence of the sparse sections 3b. Since the sparse sections 3b have spaces through which fluid can easily pass, excreted fluid rapidly permeates in the thickness direction of the absorbent body 3. These two functions ensure rapid permeation and diffusion of fluids, allowing sufficient diffusion of fluids in the planar direction within the absorbent body 3, without leaving extra absorbing power throughout the absorbent body. As a result, the amount of pulp or super-absorbent polymer used can be reduced, without lowering the absorption volume. This is advantageous from the viewpoint of economy and of alleviating environmental load.

By forming a dense/sparse structure in the absorbent body 3, the shape retention of the absorbent body 3 is increased and an effect is exhibited of minimizing twisting of the absorbent body 3 even when the wearer produces intense movement, for example.

The recesses 10 preferably have an area of 0.5 to 15 mm$^2$ and especially 1 to 10 mm$^2$, from the viewpoint of allowing effective capillary force to be designed for fluid diffusion, and avoiding excessively high rigidity against bending of the napkin as a whole, or in other words, avoiding an uncomfortable feeling for the wearer or anxiety in regard to fitting. The recesses 10 preferably have shapes with low anisotropy, with an aspect ratio of nearly 1. For example, they may have polygonal shapes that are circular, rectangular or triangular. The total ratio of the area of the recesses 10 with respect to the surface facing the back sheet of the absorbent body 3 (hereunder referred to as "area ratio on the surface facing the back sheet") is 1% to 50% and especially 2% to 30%, which is preferred from the viewpoint of allowing formation of the desired dense/sparse structure on the absorbent body 3.

The recesses 10 preferably have a pitch of 3 to 10 mm and especially 3 to 7 mm in the lengthwise direction of the absorbent article 1, and a pitch of 3 to 10 mm and especially 3 to 7 mm in the widthwise direction of the absorbent article 1, from the viewpoint of obtaining capillary force effective for fluid diffusion and spaces to facilitate fluid permeation, and of achieving rapid permeation and diffusion of fluids by these two functions to allow the absorbing power of the absorbent body as a whole to be exhibited without excess.

In order to provide recesses 10 on the surface facing the back of the absorbent body 3 sheet, a dense/sparse structure is formed in the absorbent body 3 while the surface facing the top sheet of the absorbent body 3 is essentially a flat surface. As a result, adhesiveness between the absorbent body 3 and the top sheet 2 is increased, and migration of fluid from the top sheet 2 to the absorbent body 3 is rendered even more rapid. From this viewpoint, as explained below, it is preferred for the clothing side surface of the top sheet 2 (that is, the surface facing the absorbent body) to be essentially flat.

The pressure bonded sections 9 are formed by integrally compressing the top sheet 2 and the absorbent body 3. The pressure bonded sections 9 are formed by embossing of the absorbent body 3 together with the top sheet 2, from the surface facing the top sheet of the absorbent body 3. In the pressure bonded sections 9, the top sheet 2 is pressed by an embossing pin (not shown), and the entirety of the top sheet 2 in the thickness direction introverts into the absorbent body 3, while the top sheet 2 becomes bonded and fixed to the absorbent body 3 at the introverted sections. Thus, the top sheet 2 is fixed to the absorbent body 3 with tension between the pressure bonded sections. The action of the tension maintains satisfactory adhesiveness between the top sheet 2 and the absorbent body 3 even with deformation to the absorbent article 1 by movement of the body during wearing, and fluids excreted onto the top sheet 2 rapidly migrate into the absorbent body 3 and are absorbed. Joining of the top sheet 2 and the absorbent body 3 may also be accomplished by bonding between the constituent fibers using heat fusion or an adhesive.

High density/low density sections may also be alternatingly arranged in the pressure bonded sections 9. This is effective for alleviating the rigid feel of the pressure bonded sections 9, increasing the fitting property and increasing the attractive force for fluid.

In addition, embossed sections 6' are formed across the entire surrounding portion outside the region in which the pressure bonded sections 9 are formed, or continuous embossed sections 6' are formed on both the forward and rear or right and left sides of the region, such that the pressure bonded sections 9 become positioned by the embossed sections 6' and the top sheet 2 and absorbent body 3 become even more closely adhered. As a result, migration of menstrual blood is promoted, and fluid leakage is minimized. The details regarding the embossed sections 6' will be explained below.

The arrangement pattern for the pressure bonded sections 9 and the recesses 10 are not particularly restricted. As illustrated, the pressure bonded sections 9 are arranged roughly longitudinally in the lengthwise direction of the product, further increasing the leakage-preventing effect. Also, while not shown here, the pressure bonded sections 9 may be arranged roughly longitudinally in the widthwise direction of the product to promote bending of the product and increase the fitting property on the body. The recesses 10 may also be arranged regularly at equal spacings across the entire absorbent body, or they may be arranged as desired in the lengthwise direction and widthwise direction of the product.

There are no particular restrictions on the relative arrangement pattern of the pressure bonded sections 9 and the recesses 10, but it is particularly preferred to form a plurality of recesses 10 on the surface facing the back sheet of the absorbent body 3, below the pressure bonded sections 9, and to form a dense/sparse structure across the in-plane direction of the absorbent body 3. This can further promote diffusibility of fluids in the absorbent body 3. It also further promotes permeability of fluids in the absorbent body.

As explained below, since the top sheet 2 has stretchability and the top sheet 2 is integrated with the absorbent body 3 while stretching, bonding is produced to a deeper location in the thickness direction of the absorbent body 3. Thus, adhesiveness between the top sheet 2 and the absorbent body 3 is further increased, and fluid excreted onto the top sheet 2 migrates even more rapidly through the pressure bonded sections into the absorbent body 3. Furthermore, since the top sheet 2 is resistant to separation from the absorbent body 3 at the pressure bonded sections, the structural stability is excellent against bodily movement. In the absorbent article 1 of this embodiment, this effect can prevent fluid residue and fluid flow on the top sheet, exhibiting excellent absorption performance and leakproof performance, while also producing a comfortable feel during wear with reduced feeling of wetness.

For these reasons, the pressure bonded sections 9 must be formed in the region of the absorbent article 1 facing the excretory opening, but more preferably the pressure bonded sections 9 are formed only in the region facing the excretory opening. When the pressure bonded sections 9 are formed over the entire absorbent article 1, the fitting property of the absorbent article 1 decreases and leakage tends to occur, due to the increased rigidity of the absorbent article 1.

As shown in FIG. 1, the pressure bonded sections 9 preferably extend in the lengthwise direction of the absorbent article 1. This causes excreted fluid to be guided along the pressure bonded sections 9 and flow in the lengthwise direction of the absorbent article 1, preventing fluid leakage from the side sections of the absorbent article 1. An additional advantage is that the fitting property is increased without losing flexibility in the widthwise direction of the absorbent article 1. The lengths of the pressure bonded sections 9 are preferably 5 to 20 mm and especially 5 to 10 mm.

The area of the pressure bonded sections 9 is preferably 1 to 20 $mm^2$ and especially 5 to 10 $mm^2$, from the viewpoint of allowing the fluid excreted onto the top sheet 2 to migrate more rapidly into the absorbent body 3, and preventing separation of the top sheet 2 from the absorbent body. The total ratio of the area of the pressure bonded sections 9 with respect to the surface facing the top sheet of the absorbent body 3 (hereunder referred to as "area ratio on the surface facing the top sheet") is preferably a low value of 0.01% to 2.0% and especially 0.05% to 1.0%, which is preferred from the viewpoint of preventing excessive increase in rigidity of the absorbent body 3.

The pressure bonded sections 9 preferably have a pitch of 5 to 50 mm and especially 5 to 30 mm in the lengthwise direction of the absorbent article 1, from the viewpoint of facilitating bending of the napkin as a whole, thus allowing the napkin to fit on the body more easily. Also, the pitch in the widthwise direction of the absorbent article 1 is preferably 5 to 30 mm and especially 5 to 20 mm from the viewpoint of satisfactory adhesiveness of the top sheet 2 to the absorbent body 3, more rapid migration of excreted fluids to the absorbent body 3, and avoiding rigidity that can create discomfort for the wearer.

In the absorbent article 1 of the invention, the area ratio on the surface facing the back sheet is higher than the area ratio on the surface facing the top sheet. This can satisfactorily increase attraction of fluids. From this viewpoint, the value of (area ratio on the surface facing the back sheet)/(area ratio on the surface facing the top sheet) is preferably 2-900 and especially 10-500. The actual values for the area ratio on the surface facing the back sheet and the area ratio on the surface facing the top sheet are as described above.

For the same reason as for the area ratio, in both the lengthwise direction and/or the widthwise direction of the absorbent article 1 of the invention, preferably the pitch between the pressure bonded sections 9 formed on the surface facing the top sheet is greater than the pitch between the recesses 10 formed on the surface facing the back sheet.

As shown in FIG. 1, embossed sections 6' are formed in the region of the absorbent article 1 facing the excretory opening, separately from the pressure bonded sections 9. The embossed sections 6' are located on both sides of the center section of the region facing the excretory opening in which the pressure bonded sections 9 are formed, and have closed shapes surrounding the pressure bonded sections 9. The embossed sections 6' are formed by continuous bonding between the top sheet 2 and the absorbent body 3 on the skin contact surface side of the absorbent article 1. The embossed sections 6' are also formed by embossing, similar to the pressure bonded sections 9.

By having the embossed sections 6' formed outside of the side sections of the pressure bonded sections 9, the top sheet 2 will become bonded with the absorbent body 3 while being stretched, not only between the pressure bonded sections but also between the pressure bonded sections 9 and the embossed sections 6'. As a result, adhesiveness between the top sheet 2 and the absorbent body 3 is improved, not only between the pressure bonded sections but also between the pressure bonded sections 9 and the embossed sections 6', and fluid excreted onto the top sheet 2 more rapidly migrates into the absorbent body 3 and is absorbed. In order to obtain this effect even more notably, preferably during production of the absorbent article 1 the embossed sections 6' are formed first, and then the pressure bonded sections are formed. This is because such a procedure will effectively apply tension to the top sheet 2 while bonding the top sheet 2 and the absorbent body 3.

As shown in FIG. 2, the recesses 10 are formed to the same depth at all locations of the absorbent body 3, but the depths may be changed for different locations of the absorbent body 3. The same applies for the pressure bonded sections 9. This has the advantage of improving the flexibility and fitting property of the napkin while obtaining the desired absorption capacity.

The top sheet 2 of the absorbent article 1 of the invention preferably has a plurality of projections on the skin side surface, as mentioned above. The projections may be formed as islands across the entire skin side surface of the top sheet 2. The top sheet 2 is composed of a fiber material, such as a nonwoven fabric, the projections being filled with fibers. By forming a plurality of projections, excreted fluids more easily flow into the recesses between the projections, and the fluids are rapidly removed from the skin side surface of the top sheet 2. Also, the top sheet 2 has high compression recoverability in the thickness direction, and exhibits a satisfactory cushion feel. Furthermore, since the contact area with skin is reduced, mustiness is prevented and the feeling of dryness is further increased. From these viewpoints, the projections preferably have heights of 0.3 to 5 mm and especially 0.5 to 3 mm. Also, when the top sheet is viewed flat, the projections 11 preferably have an area of 0.5 to 10 mm$^2$ and especially 1 to 5 mm$^2$.

On the other hand, the clothing side surface of the top sheet 2 is flatter than the skin side surface. Specifically, the clothing side surface of the top sheet 2 is essentially flat, or even if it is not flat, it is flatter than the skin side surface of the top sheet 2. Because of this, and the fact that the surface facing the top sheet of the absorbent body 3 is flat, adhesiveness between the top sheet 2 and the absorbent body 3 is improved.

From the viewpoint of further increasing adhesiveness between the top sheet 2 and the absorbent body 3, as mentioned above, the top sheet 2 preferably has stretchability, but it may also be one that is commonly used in the technical field, without any particular restrictions. In order to impart stretchability to the top sheet 2, the constituent fibers used for the top sheet 2 may be, for example, elastic fibers whose material itself exhibits stretchability, or fibers exhibiting stretchability by having a specific spatial configuration, such as solid crimped fibers. Elastic fibers whose material itself exhibits stretchability include fibers obtained using a synthetic rubber, such as styrene-butadiene, butadiene, isoprene or neoprene or an elastomer material, such as natural rubber, obtained by melt spinning, or synthetic fibers composed of polyurethane or polyester, such as spandex. As fibers that exhibit stretchability by having a specific spatial configuration there are particularly preferred solid crimped fibers crimped into a spiral form. For example, there may be mentioned latent crimping fibers that exhibit spiral crimping by heat treatment. In addition, there may be mentioned sheet-like materials having a structure that allows passage of fluids, such as porous films, woven fabrics or nonwoven fabrics. The fibers composing such a woven fabric or nonwoven fabric may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers composed of PE and PP graft polymers. Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

The top sheet 2 preferably has a gradually densifying structure from the skin side surface of the top sheet toward the clothing side surface of the top sheet. This further increases attraction for fluids, so that fluids rapidly migrate to the absorbent body 3. In this case, the structure may be a continuous densified structure from the skin side surface toward the clothing side surface, or it may be a stepwise-densified structure. For the same reason, the top sheet 2 preferably has gradually increasing hydrophilicity from the skin side surface toward the clothing side surface. In this case, it may be continuously increasing hydrophilicity from the skin side surface toward the clothing side surface, or it may be stepwise increasing hydrophilicity.

In order to produce a structure which gradually densifies from the skin side surface to the clothing side surface of the top sheet 2, for example, the top sheet 2 may be formed as a multilayer structure with two or more layers, with layers of increasingly higher fiber density toward the lower layers. Similarly, in order to produce a structure with gradually increasing hydrophilicity from the skin side surface to the clothing side surface of the top sheet 2, for example, the top sheet 2 may be formed as a multilayer structure with two or more layers, with layers of increasingly high hydrophilicity toward the lower layers. In regarding to hydrophilicity, it preferably has a property of being resistant to reduction in hydrophilicity with repeated absorption of fluids, or in other words, it has stable and durable hydrophilicity.

Specific examples for a top sheet 2 preferred for use in the absorbent article 1 of the invention include the sheets described in Japanese Unexamined Patent Publication No. 2002-165830, Japanese Unexamined Patent Publication No. 2002-187228, Japanese Unexamined Patent Publication No. 2003-126147, Japanese Unexamined Patent Publication No. 2003-247155, Japanese Unexamined Patent Publication No. 2003-250836 and elsewhere.

A first example of the absorbent body 3 is one having an absorbent core covered with a core wrap. Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super-absorbent polymer, such as granules of a sodium acrylate copolymer or the like.

The core wrap is not particularly restricted so long as it is a substance that is liquid-permeable and with a barrier property that does not allow permeation of the polymer absorbent body, and it may be a woven fabric or nonwoven fabric, for example. The woven fabric or nonwoven fabric may be made of a natural fiber, chemical fiber, tissue, or the like.

A second example of the absorbent body 3 is one formed from an absorbing sheet or polymer sheet, with a thickness of preferably about 0.3 to about 5.0 mm. The absorbing sheet or polymer sheet may usually be used without any particular restrictions so long as it is one that can be used in an absorbent article, such as a sanitary napkin.

As the back sheet 8 there may be mentioned films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m$^2$, for example, is preferred.

The side sheet 5 may be any of the same examples as for the liquid-permeable top sheet. The side flaps 4 can be formed from a side sheet 5 and a liquid-impermeable back sheet 8, and optionally it may have a reinforcing sheet, such as paper, between them.

When the liquid-permeable top sheet 2 is formed from a nonwoven fabric or woven fabric, the blood slipping agent 11 or blood slipping agent-containing composition 11 preferably does not obstruct the voids between the fibers of the nonwoven fabric or woven fabric, and for example, the blood slipping agent 11 or blood slipping agent-containing composition 11 may be attached as droplets or particulates on the surface of the nonwoven fabric or woven fabric fibers, or it may be covering the surfaces of the fibers.

On the other hand, when the liquid-permeable top sheet is formed of a porous film, the blood slipping agent 11 or blood slipping agent-containing composition 11 preferably does not occlude the pores of the porous film, and for example, the blood slipping agent 11 or the blood slipping agent-containing composition 11 may either be attached to the surface of the porous film as droplets or particulates, or it may cover the surface of the film without occluding the pores. This is because if the blood slipping agent 11 or blood slipping agent-containing composition 11 obstructs the holes in the porous film, migration of the absorbed liquid into the absorbent body may be inhibited.

Furthermore, in order for the blood slipping agent 11 or blood slipping agent-containing composition 11 to slip down together with the absorbed menstrual blood, it preferably has a large surface area, and a blood slipping agent 11 or blood slipping agent-containing composition 11 present as droplets or particulates preferably has a small droplet/particle diameter. According to still another embodiment of the absorbent article of the invention, the absorbent article has an absorbent body comprising a blood slipping agent 11 or a blood slipping agent-containing composition 11.

When the material coated with the blood slipping agent 11 or blood slipping agent-containing composition 11, for example, a top sheet, is a nonwoven fabric or woven fabric formed from a synthetic resin, or a porous film or the like, it is preferably subjected to hydrophilicizing treatment. The hydrophilicizing treatment may involve coating the surfaces of the fibers of the nonwoven fabric or woven fabric or the surface of the porous film with a hydrophilic agent, or mixing a hydrophilic agent with the synthetic resin used as the starting material for the nonwoven fabric or woven fabric or porous film.

This is because, if the material before coating of the blood slipping agent 11 or blood slipping agent-containing composition 11 is hydrophilic, there will be lipophilic regions due to the blood slipping agent and hydrophilic regions due to the hydrophilic agent, that are sparsely dispersed on the top sheet 2, which will allow the blood slipping agent or blood slipping agent-containing composition to exhibit slipping performance and will facilitate rapid migration of menstrual blood into the absorbent body.

The blood slipping agent 11 or blood slipping agent-containing composition 11 also has an effect as a lubricant. Thus, when the top sheet 2 is a nonwoven fabric or woven fabric, the blood slipping agent or blood slipping agent-containing composition can have reduced friction between the fibers and improved flexibility. When the top sheet is a resin film, the blood slipping agent or blood slipping agent-containing composition can have reduced friction between the top sheet and the skin.

<Method for Producing Absorbent Article>

An embodiment of a method for producing an absorbent article 1 of the invention will now be described, using a method for producing a sanitary napkin as an example. The production apparatus 100 shown in FIG. 3 was used.

Recesses 124 are formed at a prescribed pitch in the circumferential direction on the peripheral surface of a suction drum 120 rotating in the machine direction MD, as a molding form in which the absorbent body material 122 is to be packed. When the suction drum 120 is rotated and the recesses 124 approach the material feeder 121, the suction section 126 acts on the recesses 124 and the absorbent body material 122 supplied from the material feeder 121 is vacuum suctioned into the recesses 124. The material feeder 121 is formed to cover the suction drum 120, and the material feeder 121 supplies the absorbent body material 122 into the recesses 124 by air transport, forming an absorbent body 3 in the recesses 124. The absorbent body 3 formed in the recesses 124 is transferred onto a carrier sheet 110 advancing in the machine direction MD.

Embossing is carried out from one surface of the absorbent body 3 (the surface facing the back sheet). Recesses 10 are formed in the layered body 262 by passing between a lower roll 132-1 having a plurality of protruding pins planted around the peripheral surface in a regular manner (not shown), and an upper roll 131-1 as a smooth roll, as the embossing apparatus 130. During embossing, the roll may be heated to a prescribed temperature so that the recesses 10 are formed in an effective manner.

While not shown in the drawing, the carrier sheet 110 supports the layered body 262 by two belts extending on both sides toward the machine direction (MD direction). That is, both edge sections (both end sections) extending on both sides in the machine direction (MD direction), of the surface on the carrier sheet 110 side of the layered body 262 the bottom side in FIG. 3), are supported by the carrier sheet 110, but the center section extending toward the machine direction (MD direction) is not supported on the carrier sheet 110 but is exposed between the two belts of the carrier sheet 110. The exposed sections are embossed. Thus, the layered body 262 is embossed by the embossing apparatus 130 (upper roll 131-1 and lower roll 132-1) while mounted on the carrier sheet 110.

The top sheet 2 supplied from the roll 210 is layered on the absorbent body 3, forming a layered body 262. The layered body 262 is subjected to embossing, forming embossed sections 6' by hot pressing on the top sheet 2 and the absorbent body 3. The embossing is accomplished, for example, by inserting the layered body 262 between a roll with irregularities (not shown) having annular protrusions corresponding to the embossed sections 6' formed on the peripheral surface, and a receiving roll having a peripheral surface made of a surface-smooth elastic solid. Specifically, the embossed sections 6' are formed on the layered body 262 by passing between the upper roll 131-2 and lower roll 132-2 of the embossing apparatus 130.

Next, the interior area of the embossed sections 6' of the layered body 262 on which the embossed sections 6' have been formed is subjected to embossing to form pressure bonded sections 9. The embossing is accomplished by inserting the layered body 262 between a roll with a plurality of protruding pins planted in a regular manner on the peripheral surface (not shown), and a smooth roll. Specifically, pressure bonded sections 9 are formed on the layered body 262 by passing between the upper roll 131-3 and lower roll 132-3 of the embossing apparatus 130.

Next, the back sheet 8 that has been reeled out from a back sheet roll 140 is coated with an adhesive from an adhesive coater, and the back sheet 8 and layered body 262 are layered to form a layered body 263. Next, the layered body 263 is formed into the shape of an absorbent article by round embossing with an embossing roll 261 (not shown), and a cutter 150 is used to cut it into the shape of the absorbent article 1 (sanitary napkin).

A coating spray 160 of the blood slipping agent 11 or blood slipping agent-containing composition 11 is used to coat the blood slipping agent 161 onto the center region of the absorbent article 1 (sanitary napkin), to form a blood slipping agent layer on the skin side surface of the top sheet 2. In this manner it is possible to produce an absorbent article 1 (sanitary napkin).

The blood slipping agent layer is preferably formed in at least the excretory opening contact region in the excreta-supply region of the top sheet 2.

In the method for producing an absorbent article according to the invention, the blood slipping agent was coated after cutting out the absorbent article 1 (sanitary napkin), but it may instead be coated at any stage before cutting, or it may be coated during the production steps for the top sheet 2. In order to prevent dripping down of the blood slipping agent that has been coated during production, the blood slipping agent is preferably coated at a downstream stage of the production process, such as immediately before packaging of the absorbent article 1 (sanitary napkin).

There are no particular restrictions on the method of applying the blood slipping agent or blood slipping agent-containing composition, or the coating solution containing it, and if necessary the blood slipping agent or blood slipping agent-containing composition or the coating solution containing it may be heated, and a coating applicator, for example a non-contact coater, such as a spiral coater, curtain coater, spray coater or dip coater, or a contact coater, may be used for application of the blood slipping agent or blood slipping agent-containing composition or the coating solution containing it. The coating applicator is preferably a non-contact coater, from the viewpoint of uniformly dispersing the droplet or particulate modifying agent throughout, and from the viewpoint of not causing damage in the material.

The blood slipping agent or blood slipping agent-containing composition, or the coating solution containing it, may be coated directly, if it is a liquid at room temperature, or it may be heated to lower the viscosity, and when it is a solid at room temperature, it may be heated to liquefaction and coated from a control seam HMA (Hot Melt Adhesive) gun. By increasing the air pressure of the control seam HMA gun, it is possible to apply the blood slipping agent or blood slipping agent-containing composition as fine particulates. The coating amount of the blood modifying agent or blood slipping agent-containing composition can be adjusted, for example, by adjusting the discharged amount from a control seam HMA gun.

The blood slipping agent or blood slipping agent-containing composition may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent or blood slipping agent-containing composition will be lowered, thereby allowing the application steps to be simplified, facilitating application and making heating during application unnecessary.

According to the method for producing an absorbent article 1 of the invention, pressure bonded sections 9 are formed in the interior area of both embossed sections 6' after forming the embossed sections 6', such that strong tension is naturally applied to the top sheet 2 and the top sheet 2 is anchored to the absorbent body 3 in that state. Furthermore, since the top sheet is bonded to the absorbent body while being highly stretched at the pressure bonded sections 9, powerful bonding strength is obtained and adhesiveness between the top sheet 2 and the absorbent body 3 is further improved at the sections other than the pressure bonded sections 9.

The above explanation concerned one embodiment of the method for producing an absorbent article according to the invention, but the invention is not restricted to that embodiment. For example, the top sheet 2 of the embodiment was a flat sheet on both the skin side surface and the clothing side surface, but it may instead have a plurality of projections on the skin side surface.

Also, in this embodiment of the method for producing an absorbent article according to the invention, the pressure bonded sections 9 may be formed before forming the embossed sections 6', so that the embossed sections 6' are formed afterwards.

EXAMPLES

The invention will now be explained by examples, with the understanding that the invention is not meant to be limited to the examples.

Test Example 1

[Evaluation of Rewetting Rate and Absorbent Body Migration Rate]

A commercially available sanitary napkin having the shape shown in FIG. 1 (not coated with a blood slipping agent) was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood slipping agents used for testing are listed below.
[($a_1$) Ester of a Chain Hydrocarbon Tetraol and at Least One Fatty Acid]

UNISTAR H-408BRS, product of NOF Corp.

Pentaerythritol tetra(2-ethylhexanoate), weight-average molecular weight: approximately 640

UNISTAR H-2408BRS-22, product of NOF Corp.

Mixture of pentaerythritol tetra(2-ethylhexanoate) and neopentylglycol di(2-ethylhexanoate) (58:42 as mass ratio), weight-average molecular weight: approximately 520
[($a_2$) Ester of a Chain Hydrocarbon Triol and at Least One Fatty Acid]

Cetiol SB45DEO, Cognis Japan

Glycerin and fatty acid triester, with oleic acid or stearylic acid as the fatty acid.

SOY42, product of NOF Corp.

Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.

Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.

Glycerin and fatty acid triester with $C_8$ fatty acid:$C_{12}$ fatty acid at a mass ratio of about 44:56, weight-average molecular weight: approximately 570

PANACET 810s, product of NOF Corp.

Glycerin and fatty acid triester with $C_8$ fatty acid:$C_{10}$ fatty acid at a mass ratio of about 85:15, weight-average molecular weight: approximately 480

PANACET 800, product of NOF Corp.

Glycerin and fatty acid triester with octanoic acid ($C_8$) as the entire fatty acid portion, weight-average molecular weight: approximately 470

PANACET 800B, product of NOF Corp.

Glycerin and fatty acid triester with 2-ethylhexanoic acid ($C_8$) as the entire fatty acid portion, weight-average molecular weight: approximately 470

NA36, product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.

Glycerin and fatty acid triester with $C_8$ fatty acid:$C_{10}$ fatty acid:$C_{12}$ fatty acid:$C_{14}$ fatty acid: $C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.

Glycerin and fatty acid diester with octanoic acid as the fatty acid, weight-average molecular weight: approximately 340

[($a_3$) Ester of a Chain Hydrocarbon Diol and at Least One Fatty Acid]

UNISTAR H-208BRS, product of NOF Corp.

Neopentyl glycol di(2-ethylhexanoate), weight-average molecular weight: approximately 360

COMPOL BL, product of NOF Corp.

Dodecanoic acid ($C_{12}$) monoester of butylene glycol, weight-average molecular weight: approximately 270

COMPOL BS, product of NOF Corp.

Octadecanoic acid ($C_{18}$) monoester of butylene glycol, weight-average molecular weight: approximately 350

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.

Weight-average molecular weight: approximately 400

Tributyl citrate, product of Tokyo Kasei Kogyo Co., Ltd.

Weight-average molecular weight: approximately 360

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl adipate, product of Wako Pure Chemical Industries, Ltd.

Weight-average molecular weight: approximately 380

[($d_3$) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_3$-$C_6$ Alkylene Glycol]

UNIOL PB500, product of NOF Corp.

Polybutylene glycol, weight-average molecular weight: approximately 500

UNIOL PB700, product of NOF Corp.

Polyoxybutylene polyoxypropylene glycol, weight-average molecular weight: approximately 700

[($f_1$) Chain Alkane]

PARLEAM 6, product of NOF Corp.

Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL PB1000R, product of NOF Corp.

Polybutylene glycol, weight-average molecular weight: approximately 1,000

UNIOL D-250, product of NOF Corp.

Polypropylene glycol, weight-average molecular weight: approximately 250

UNIOL D-400, product of NOF Corp.

Polypropylene glycol, weight-average molecular weight: approximately 400

UNIOL D-700, product of NOF Corp.

Polypropylene glycol, weight-average molecular weight: approximately 700

UNIOL D-1000, product of NOF Corp.

Polypropylene glycol, weight-average molecular weight: approximately 1,000

UNIOL D-1200, product of NOF Corp.

Polypropylene glycol, weight-average molecular weight: approximately 1,160

UNIOL D-2000, product of NOF Corp.

Polypropylene glycol, weight-average molecular weight: approximately 2,030

UNIOL D-3000, product of NOF Corp.

Polypropylene glycol, weight-average molecular weight: approximately 3,000

UNIOL D-4000, product of NOF Corp.

Polypropylene glycol, weight-average molecular weight: approximately 4,000

PEG1500, product of NOF Corp.

Polyethylene glycol, weight-average molecular weight: approximately 1,500-1,600

WILBRITE cp9, product of NOF Corp.

Polybutylene glycol compound with OH groups at both ends esterified by hexadecanoic acid ($C_{16}$), weight-average molecular weight: approximately 1,150

UNILUBE MS-70K, product of NOF Corp.

Stearyl ether of polypropylene glycol, approximately 15 repeating units, weight-average molecular weight: approximately 1,140

NONION S-6, product of NOF Corp.

Polyoxyethylene monostearate, approximately 7 repeating units, weight-average molecular weight: approximately 880

UNILUBE 5TP-300 KB

Polyoxyethylenepolyoxypropylene pentaerythritol ether, produced by addition of 5 mol of ethylene oxide and 65 mol of propylene oxide to 1 mol of pentaerythritol, weight-average molecular weight: 4,130

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

The kinematic viscosities, water holding percentages, weight-average molecular weights, IOBs and melting points of the samples are shown in Table 2.

For the melting point, "<45" indicates a melting point of below 45° C.

Almost the entire skin contact surface of the top sheet of the sanitary napkin was coated with the aforementioned blood slipping agent. Each blood slipping agent was used directly, when the blood slipping agent was liquid at room temperature, or when the blood slipping agent was solid at room temperature it was heated to a temperature of its melting point 20° C., and then a control seam HMA gun was used for atomization of each blood slipping agent and coating onto the skin contact surface of the top sheet to a basis weight of about 5 g/m$^2$.

Figure 4:
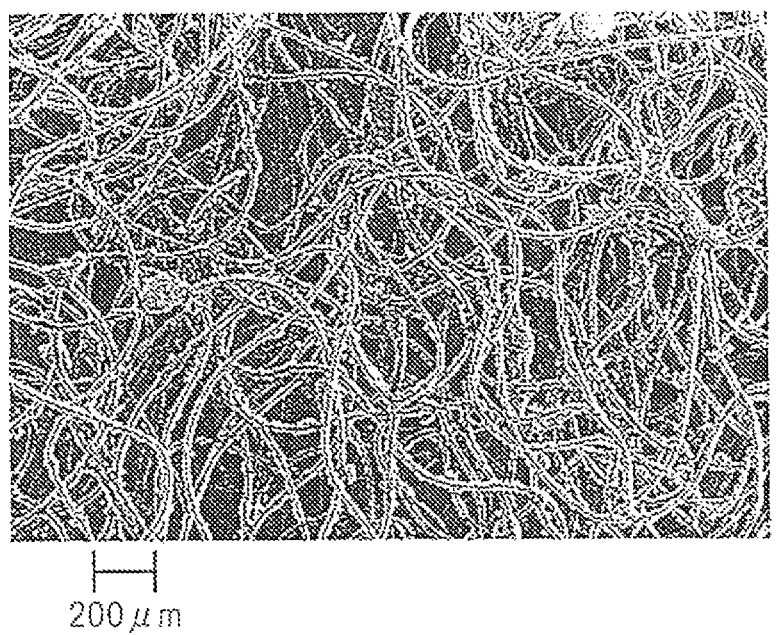
FIG. 4 is an electron micrograph of the skin contact surface of a top sheet in a sanitary napkin wherein the top sheet comprises tri-C2L oil fatty acid glycerides.

FIG. 4 is an electron micrograph of the skin contact surface of a top sheet in a sanitary napkin (No. 1-5) wherein the top sheet comprises tri-C2L oil fatty acid glycerides. As clearly seen in FIG. 4, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood slipping agent, and 3 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Qualitative filter paper No. 2, product of Advantech Toyo, Inc., 50 mm×35 mm) were placed on the location where the blood had been dropped, and then a weight was placed thereover to a pressure of 30 g/cm$^2$. After 1 minute, the filter paper was removed and the "rewetting rate" was calculated by the following formula.

Rewetting rate(%)=100×(filter paper mass after test– initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet (TS) after the absorbent body migration rate test was visually evaluated on the following scale.

VG (Very Good): Virtually no redness of blood remaining, and no clear delineation between areas with and without blood.

G (Good): Slight redness of blood remaining, but difficult to discriminate between areas with and without blood.

F (Fair): Slight redness of blood remaining, areas with blood discernible.

P (Poor): Redness of blood completely remaining.

The tack on the skin contact surface of the top sheet was also measured at 35° C., and evaluated on the following scale.

G: No tack
F: Slight tack
P: Tack

The results are summarized in Table 2 below.

TABLE 2

| No. | Blood slipping agent | Kinematic viscosity (mm$^2$/s, 40° C.) | Water holding percentage (mass %) | Weight-average molecular weight | IOB | Melting point (° C.) | Rewetting rate (%) | Absorbent body migration speed (sec) | TS whiteness | Tack |
|---|---|---|---|---|---|---|---|---|---|---|
| 1-1 | H-408 BRS | 45 | 0.7 | 640 | 0.13 | <–5 | 1.2 | 3 | VG | G |
| 1-2 | H-2408 BRS-22 | 22 | 0.8 | 520 | 0.18 | <–5 | 2.0 | 3 | VG | G |
| 1-3 | Cetiol SB45DEO | | | | 0.16 | 44 | 7.0 | 6 | VG | |
| 1-4 | SOY42 | | | 880 | 0.16 | 43 | 5.8 | 8 | VG | |
| 1-5 | Tri-C2L oil fatty acid glyceride | 20 | <1.0 | 570 | 0.27 | 37 | 0.3 | 3 | VG | G |
| 1-6 | Tri-CL oil fatty acid glyceride | 15 | <1.0 | 570 | 0.28 | 38 | 1.7 | 3 | VG | G |
| 1-7 | PANACET 810s | 9 | 0.3 | 480 | 0.32 | –5 | 2.8 | 3 | VG | G |
| 1-8 | PANACET 800 | 15 | 0.5 | 470 | 0.33 | –5 | 0.3 | 3 | VG | G |
| 1-9 | PANACET 800B | 20 | <1.0 | 470 | 0.33 | –5 | 2.0 | 3 | VG | G |
| 1-10 | NA36 | 40 | <1.0 | 880 | 0.16 | 37 | 3.9 | 5 | VG | G |
| 1-11 | Tri-coconut oil fatty acid glyceride | 25 | <1.0 | 670 | 0.28 | 30 | 4.3 | 5 | VG | G |
| 1-12 | Caprylic acid diglyceride | 25 | 2.7 | 340 | 0.58 | <45 | 4.2 | 9 | G | G |
| 1-13 | UNISTAR H-208BRS | 8 | 0.7 | 360 | 0.24 | <–5 | 2.0 | 5 | VG | G |
| 1-14 | COMPOL BL | 10 | 1.6 | 270 | 0.50 | 2 | 2.0 | 5 | G | G |
| 1-15 | COMPOL BS | 35 | 0.3 | 350 | 0.36 | 37 | 7.9 | 9 | G | G |
| 1-16 | Tributyl O-acetylcitrate | 15 | 0.9 | 400 | 0.60 | <45 | 6.2 | 8 | VG | G |
| 1-17 | Tributyl citrate | 12 | 0.6 | 360 | 0.78 | <45 | 3.0 | 6 | G | G |
| 1-18 | Dioctyl adipate | 7 | 0.4 | 380 | 0.27 | <45 | 1.7 | 6 | VG | G |
| 1-19 | ELECTOL WE20 | 10 | 0.3 | 360 | 0.13 | 29 | 1.8 | 5 | VG | G |

TABLE 2-continued

| No. | Blood slipping agent | Kinematic viscosity (mm²/s, 40° C.) | Water holding percentage (mass %) | Weight-average molecular weight | IOB | Melting point (° C.) | Rewetting rate (%) | Absorbent body migration speed (sec) | TS whiteness | Tack |
|---|---|---|---|---|---|---|---|---|---|---|
| 1-20 | ELECTOL WE40 | 15 | 0.5 | 390 | 0.12 | 37 | 1.8 | 4 | VG | G |
| 1-21 | UNIOL PB500 | 40 | 3.6 | 500 | 0.44 | <45 | 4.5 | 4 | G | G |
| 1-22 | UNIOL PB700 | 50 | 2.3 | 700 | 0.49 | −5 | 2.8 | 5 | G | G |
| 1-23 | PARLEAM 6 | 5 | 0.06 | 330 | 0.00 | −5 | 6.0 | 8 | VG | G |
| 1-24 | NA50 | 80<< | —* | 880 | 0.18 | 52 | 15.5 | 60 | P | G |
| 1-25 | (Caprylic acid/capric acid) monoglyceride | 70 | 4.0<< | 220 | 1.15 | <45 | 4.0 | 4 | P | G |
| 1-26 | 90-L2 lauric acid monoglyceride | 80<< | 4.0<< | <1,000 | 0.87 | 58 | 6.2 | 7 | P | G |
| 1-27 | Isopropyl citrate | 120 | 4.0<< | 230 | 1.56 | <45 | 12.2 | 5 | G | F |
| 1-28 | Diisostearyl malate | 450 | 4.0<< | 640 | 0.28 | <45 | 5.5 | 8 | F | F |
| 1-29 | UNIOL PB1000R | 70 | 5.5 | 1000 | 0.40 | <45 | 4.0 | 4 | G | F |
| 1-30 | UNIOL D-250 | 20 | 4.0<< | 250 | | <45 | — | — | P | G |
| 1-31 | UNIOL D-400 | 30 | 4.0<< | 400 | 0.76 | <45 | 8.7 | 40 | P | G |
| 1-32 | UNIOL D-700 | 50 | 34.6 | 700 | 0.58 | <45 | 7.5 | — | F | G |
| 1-33 | UNIOL D-1000 | 70 | 26.7 | 1,000 | 0.51 | <45 | 6.8 | 15 | F | F |
| 1-34 | UNIOL D-1200 | 90 | 16.2 | 1,160 | 0.48 | <45 | 0.5 | 11 | F | F |
| 1-35 | UNIOL D-2000 | 160 | | 2,030 | | <45 | — | — | F | P |
| 1-36 | UNIOL D-3000 | | 0.6 | 3,000 | 0.39 | <45 | 1.7 | 10 | F | P |
| 1-37 | UNIOL D-4000 | 450 | 0.5 | 4,000 | 0.38 | <45 | 1.0 | 7 | G | P |
| 1-38 | PEG 1500 | 120 | 4.0<< | 1,500–1,600 | 0.78 | 40 | 11.0 | 38 | P | P |
| 1-39 | WILBRITE CP9 | 120 | 0.6 | 1,150 | 0.21 | 35 | 1.4 | 3 | G | P |
| 1-40 | UNILUBE MS-70K | 50 | 2.8 | 1,140 | 0.30 | <−10 | 6.7 | 3 | G | F |
| 1-41 | NONION S-6 | 65 | 4.0<< | 880 | 0.44 | 37 | 8.4 | 7 | P | G |
| 1-42 | UNILUBE 5TP-300KB | 310 | 3.9 | 4,130 | 0.39 | <45 | 2.0 | 6 | G | P |
| 1-43 | WILBRITE s753 | 120 | 27.3 | 960 | 0.67 | −5 | 9.3 | 9 | F | F |
| 1-44 | UNIOL TG-330 | 30 | | 330 | 1.27 | <45 | — | — | — | G |
| 1-45 | UNIOL TG-1000 | 100 | 21.2 | 1,000 | 0.61 | <45 | 14.2 | 7 | G | G |
| 1-46 | UNIOL TG-3000 | 230 | 4.3 | 3,000 | 0.42 | <45 | 0.8 | 6 | G | P |
| 1-47 | UNIOL TG-4000 | 300 | 2.4 | 4,000 | 0.40 | <45 | 2.0 | 6 | G | P |
| 1-48 | UNILUBE DGP-700 | 200 | 4.0<< | 700 | 0.91 | <0 | 8.0 | 10 | F | F |
| 1-49 | UNIOX HC60 | 1150 | | 3,570 | 0.46 | 33 | 14.6 | 46 | P | P |
| 1-50 | Vaseline | 80<< | 0.0 | <1,000 | 0.00 | 55 | 9.7 | 10 | F | P |
| 1-51 | None | — | — | — | — | — | 22.7 | 60< | P | G |

*High viscosity, unmeasurable.

In the absence of a blood slipping agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance.

Similarly, it was found that the absorption performance is greatly improved with a blood slipping agent having a kinematic viscosity of about 0.01 to 80 mm²/s at 40° C., a water holding percentage of about 0.01 to about 4.0 mass %, and a weight-average molecular weight of less than about 1,000.

Next, several volunteer subjects were asked to wear sanitary napkin Nos. 1-1 to 1-51, and the obtained responses indicated that with the sanitary napkins comprising blood slipping agent Nos. 1-1 to 1-23, the top sheets had no sticky feel and the top sheets were smooth, even after absorption of menstrual blood.

Also, with sanitary napkins that comprised blood slipping agent Nos. 1-11, 13, 16, 18-20 and 23, the skin contact surfaces of the top sheets after absorption of menstrual blood had not been reddened by the blood and the unpleasantness was minimal.

Also, the top sheet was removed from a commercially available sanitary napkin having the shape shown in FIG. 1 (not coated with a blood slipping agent), and the clothing side surface thereof was coated with the aforementioned blood slipping agent in the region indicated in FIG. 1. The blood slipping agent was coated so that the blood slipping agent-containing region contained the blood slipping agent at a basis weight of about 5 g/m², using a control seam HMA gun, with heating to a temperature of the melting point +20° C. as necessary. Upon visually confirming the top sheet coated with the blood slipping agent, the basis weight of the blood slipping agent on the clothing side surface (coated surface) was found to be greater than the basis weight of the blood slipping agent on the skin side surface (non-coated surface).

Next, the top sheet was rebonded to the absorbent body to prepare sanitary napkins No. 1'-1 (H-408BRS) to No. 1'-23 (PARLEAM 6).

Sanitary napkins No. 1'-1 (H-408BRS) to No. 1'-23 (PARLEAM 6) were thus prepared. The sanitary napkins No. 1'-1 and No. 1-1 were identical in that the blood slipping agent was H-408BRS, but the distribution of the blood slipping agent in the thickness direction of the absorbent article was different. This also applies to the other sanitary napkins.

When the sanitary napkins produced for Nos. 1'-1 to 1'-23 were worn by multiple volunteer participants, the sanitary napkins of Nos. 1'-1 to 1'-23 generally had the same performance as Nos. 1-1 to 1-23, and the responses received indicated that after menstrual blood had been absorbed, the menstrual blood was rapidly absorbed into the absorbent body within the excretory opening contact region.

This equivalent performance is partially attributed to the blood slipping agent on the clothing side surface of the top sheet having migrated onto the skin side surface by pressure applied onto the sanitary napkin by daily activities of the wearer.

Test Example 2

[Surface Residue Rate of Menstrual Blood on Top Sheet with Ridge-Furrow Structure]

The surface residue rate of menstrual blood on a top sheet with a ridge-furrow structure was evaluated.

There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, and the pitch of the ridge-furrow structure (ridge width+furrow width) was approximately 4 mm and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (a surface having ridge-furrow structure) of the top sheet from a control seam HMA gun at room temperature, to a basis weight of 5.0 g/m$^2$. With an electron microscope it was confirmed that the H-408BRS was adhering onto the fiber surfaces as fine particulates.

A back sheet, an absorbent body, a second sheet, and a top sheet with the ridge-furrow surface facing upward, were stacked in that order to form sanitary napkin No. 2-1.

Sanitary napkins No. 2-2 to No. 2-40 were produced, changing the blood slipping agent from UNISTAR H-408BRS to the ones listed in Table 3 below. Each blood slipping agent was used directly, when it was liquid at room temperature, or when the blood slipping agent was solid at room temperature it was heated to a temperature of its melting point+20° C., and then a control seam HMA gun was used for atomization of the blood slipping agent and coating onto the skin contact surface of the top sheet to a basis weight of about 5 g/m$^2$.

The blood slipping agent was coated onto essentially the entire skin contact surface of the top sheet, and on both the ridges and furrows.

[Test Methods]

After measuring the mass $W_2$ (g) of the top sheet (the mass of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of the top sheet after the test) was measured and the "surface residue rate A (mass %)" was calculated by the following formula.

Surface residue rate A(mass %)=100×[$W_3$(g)−$W_2$(g)]/4.0(g)

The results are shown in Table 3 below.

TABLE 3

| No. | Blood slipping agent | Surface residue rate (mass %) |
|---|---|---|
| 2-1 | H-408BRS | 0.8 |
| 2-2 | H-2408BRS-22 | 0.8 |
| 2-3 | PANACET 810S | 0.8 |
| 2-4 | PANACET 800 | 1.8 |
| 2-5 | Caprylic acid diglyceride | 1.0 |
| 2-6 | UNISTAR H-208BRS | 0.5 |
| 2-7 | COMPOL BL | 1.3 |
| 2-8 | COMPOL BS | 2.5 |
| 2-9 | Tributyl O-acetylcitrate | 0.5 |
| 2-10 | Tributyl acetate | 1.8 |
| 2-11 | Dioctyl adipate | 1.5 |
| 2-12 | ELECTOL WE20 | 0.5 |
| 2-13 | ELECTOL WE40 | 2.3 |
| 2-14 | UNIOL PB500 | 2.5 |
| 2-15 | UNIOL PB700 | 1.3 |
| 2-16 | PARLEAM 6 | 2.0 |
| 2-17 | NA50 | 4.3 |
| 2-18 | (Caprylic acid/Capric acid) monoglyceride | 5.0 |
| 2-19 | 90-L2 lauric acid monoglyceride | 5.0 |
| 2-20 | Isopropyl citrate | 4.8 |
| 2-21 | Diisostearyl malate | 3.3 |
| 2-22 | UNIOL PB1000R | 2.5 |
| 2-23 | UNIOL D-250 | 3.8 |
| 2-24 | UNIOL D-400 | 4.8 |
| 2-25 | UNIOL D-700 | 4.8 |
| 2-26 | UNIOL D-1000 | 3.8 |
| 2-27 | UNIOL D-1200 | 3.0 |
| 2-28 | UNIOL D-3000 | 3.0 |
| 2-29 | UNIOL D-4000 | 2.5 |
| 2-30 | PEG1500 | 5.5 |
| 2-31 | WILBRITE CP9 | 6.8 |
| 2-32 | UNILUBE MS-70K | 1.5 |
| 2-33 | UNILUBE 5TP-300KB | 2.0 |
| 2-34 | WILBRITE s753 | 3.5 |
| 2-35 | UNIOL TG-1000 | 3.5 |
| 2-36 | UNIOL TG-3000 | 1.0 |
| 2-37 | UNIOL TG-4000 | 2.0 |
| 2-38 | UNILUBE DGP-700 | 3.5 |
| 2-39 | Vaseline | 4.0 |
| 2-40 | None | 7.5 |

With sanitary napkin No. 2-40, which had no blood slipping agent, the surface residue rate was 7.5 mass %, but with sanitary napkins No. 2-1 to No. 2-16 wherein the kinematic viscosity and water holding percentage were within the prescribed ranges, the surface residue rate was 2.5 mass % or lower.

With sanitary napkins No. 2-1 to No. 2-16, it was observed that the horse EDTA blood that was dropped onto the ridges of the top sheet slid down from the ridges into the furrows, and was rapidly absorbed from the furrows into the absorbent body. However, with sanitary napkin No. 2-40 which had no blood slipping agent, the dropped horse EDTA blood did not slip down into the furrows but slowly dripped down into the furrows, most of it remaining on the ridges of the top sheet. Also, with the absorbent articles with high a water holding percentage, as with No. 2-25, for example, the horse EDTA blood that was dropped onto the ridges of the top sheet did not slip down into the furrows but slowly dripped while partially remaining on the top sheet, and a portion thereof remained on the ridges.

The following experiment was also conducted in order to confirm the function of the blood slipping agent.

Test Example 3

[Viscosity of Blood Containing Blood Slipping Agent]

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate, due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the invention has an effect of lowering the viscosity of blood, such as menstrual blood in the low viscosity range. Lowering the blood viscosity presumably allows absorbed menstrual blood to more easily migrate rapidly from the top sheet to the absorbent body.

Test Example 4

[Photomicrograph of Blood Slipping Agent-Containing] Blood

Menstrual blood was sampled from healthy volunteers onto food storage wrap film, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 5(*a*), and a photomicrograph of menstrual blood containing PANACET 810s is shown in FIG. 5(*b*).

Figure 5:
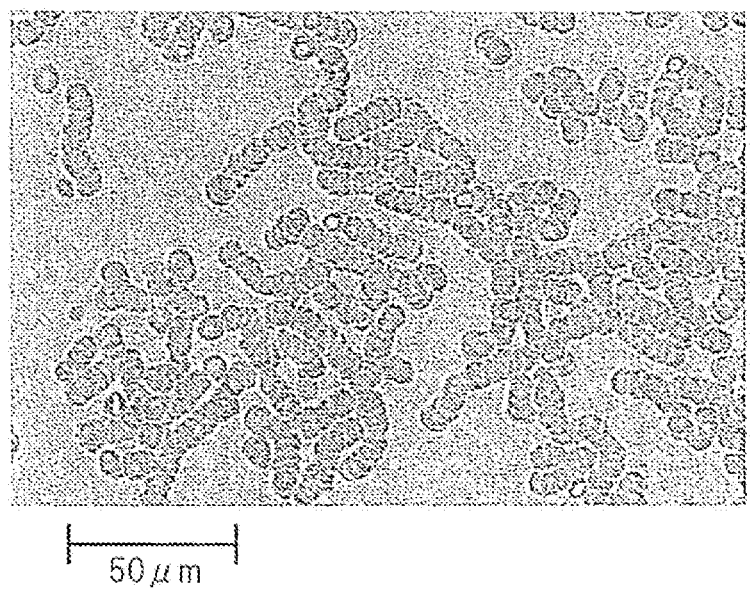
FIG. 5 is a pair of photomicrographs of menstrual blood containing and not containing a blood slipping agent.
Figure 5:
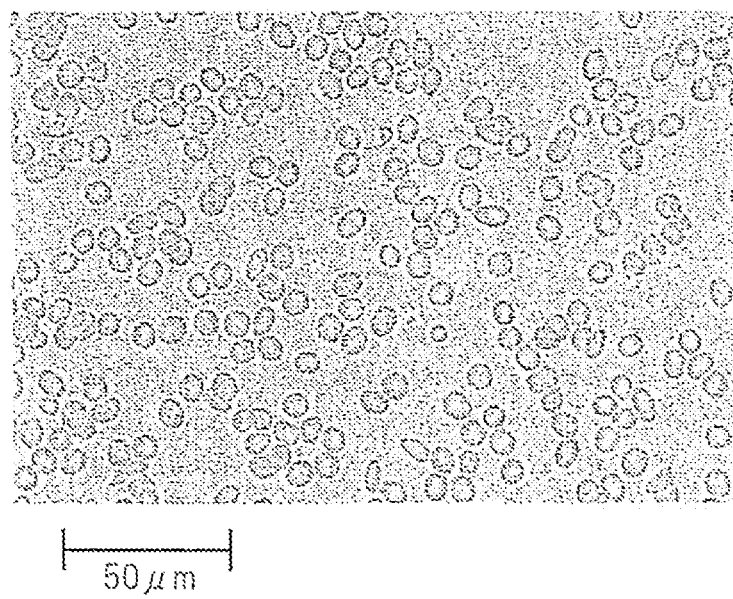

As shown in FIG. 5, the erythrocytes formed aggregates, including a rouleaux structure, in the menstrual blood containing no blood slipping agent, while the erythrocytes were stably dispersed in the menstrual blood containing PANACET 810s. This suggests that the blood slipping agent has the function of stabilizing erythrocytes in blood.

Test Example 5

[Surface Tension of Blood Containing Blood Slipping] Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 6:
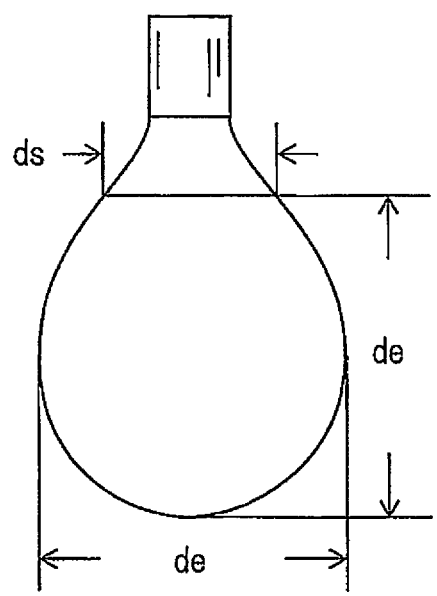
FIG. 6 is a diagram illustrating a method of measuring surface tension.

The measurement was accomplished automatically with the apparatus, and the surface tension γ was determined by the following formula (see FIG. 6).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", 5. Vibrating density test method.

The measurement was accomplished using a DA-505 by Kyoto Electronics Co., Ltd.

The results are shown in Table 4 below.

TABLE 4

| No. | Blood slipping agent | | Measuring temperature (° C.) | Surface tension (mN/m) |
| --- | --- | --- | --- | --- |
| | Type | Amount (mass %) | | |
| 1 | — | — | 35 | 62.1 |
| 2 | PANACET 810s | 0.01 | 35 | 61.5 |
| 3 | | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Based on Table 4 it is seen that the blood slipping agent has an effect of lowering the surface tension of blood.

Lowering the surface tension of blood presumably allows absorbed blood to rapidly migrate from the top sheet to the absorbent body, without being retained between the top sheet fibers.

Test Example 6

(1) Fabrication of Absorbent Articles Nos. 1 to 3

Figure 3:
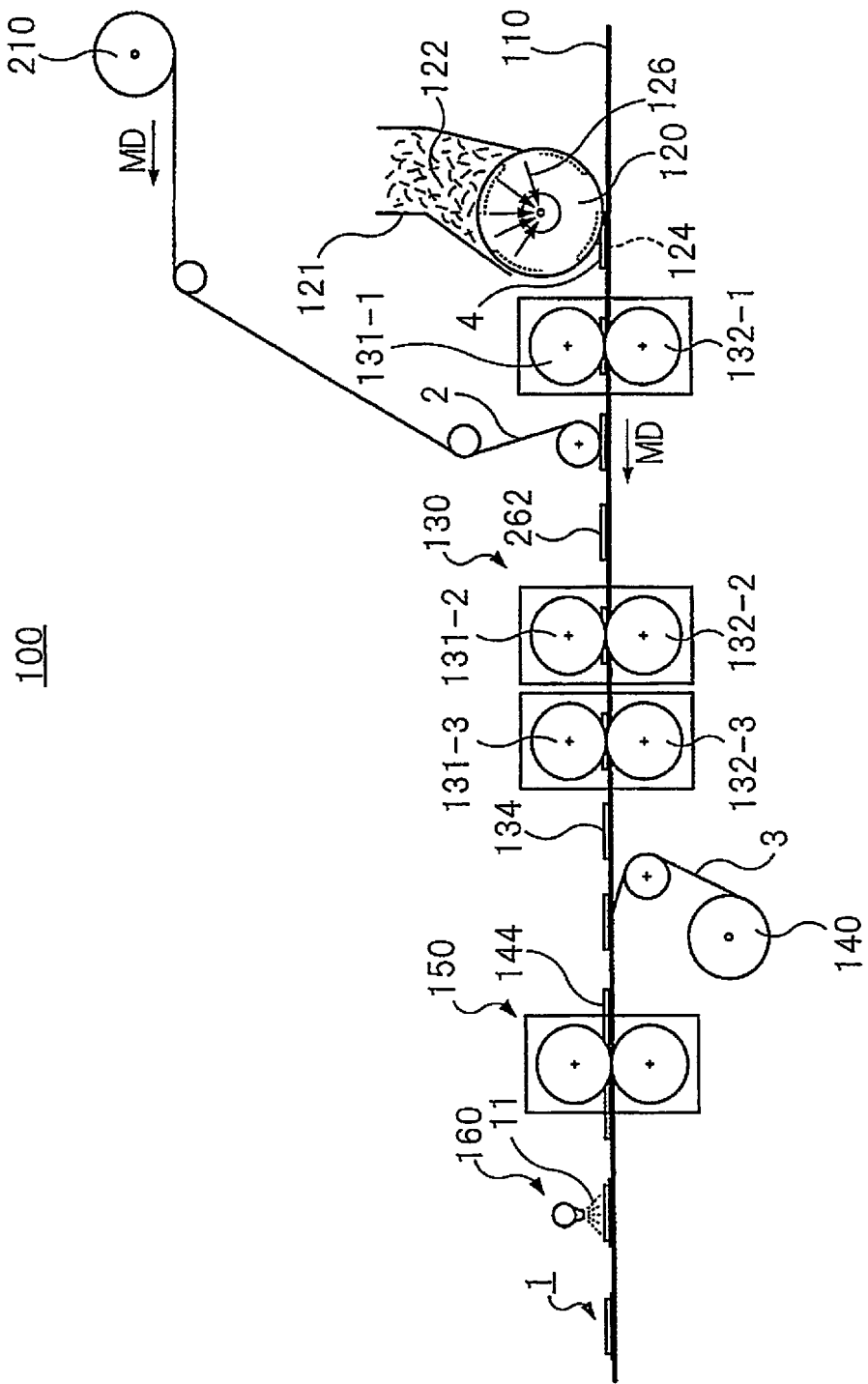
FIG. 3 is a diagram illustrating a method for producing an absorbent article 1 (sanitary napkin) of the invention.

The apparatus shown in FIG. 3 was used to produce absorbent article No. 1. For production of absorbent article No. 1, the absorbent body was layered on a top sheet and a back sheet was then layered on the layered body, and finally the skin contact surface of the top sheet (the skin side surface of the top sheet) was coated with a blood slipping agent (triglyceride) to produce absorbent article No. 1. The coating basis weight of the blood slipping agent on absorbent article sample No. 1 was 4 g/m$^2$. The specific production method was as follows. Absorbent article No. 2 was produced by the same production method as for absorbent article No. 1, except that no blood slipping agent-coating step was carried out. Absorbent article No. 3 was produced by the same production method as for absorbent article No. 1, except that the embossing step with the lower roll 132-1 and upper roll 131-1 and the embossing step with the lower roll 132-2 and upper roll 131-2 were not carried out.

(2) Measurement of Top Sheet Diffusion Length (TS Diffusion Length) and Absorbent Body Diffusion Length (AB Diffusion Length)

<Test Method>

On the skin contact surface of absorbent article Nos. 1 to 3 there was dropped 4 mL of horse EDTA blood at 37±1° C. (prepared by adding ethylenediaminetetraacetic acid (EDTA) to horse blood to prevent coagulation) for 3 seconds using a pipette (80 ml/min). After an elapse of 1 minute, the TS diffusion length (lengthwise direction and widthwise direction) and AB diffusion length (lengthwise direction and widthwise direction) were measured.

The TS diffusion length is the maximum length of horse EDTA blood in the lengthwise direction or widthwise direction of the top sheet, and the AB diffusion length is the maximum length of horse EDTA blood in the lengthwise direction or widthwise direction of the absorbent body. The lengthwise direction and widthwise direction are, respectively, the lengthwise direction and widthwise direction (direction perpendicular to the lengthwise direction) of the absorbent article.

The procedure was repeated a total of 3 times for each absorbent article, and the average value was used as the measured value.

<Results>

Figure 7:
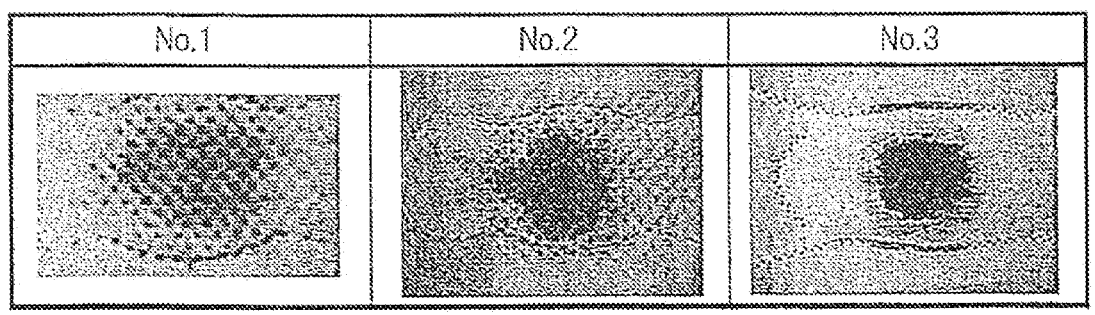
FIG. 7 is a set of photographs showing the results for Test Example 6.

The results are shown in Table 5 and FIG. 7.

As shown in Table 5, absorbent articles No. 1 and 2 had larger TS diffusion lengths in the lengthwise direction than absorbent article No. 3, due to the effect of the pressure bonded sections. Absorbent articles No. 1 and 2 had larger AB diffusion lengths in both the lengthwise direction and widthwise direction compared to absorbent article No. 3, due to the effect of the pressure bonded sections and the recesses of the absorbent body.

In FIG. 7, the left-right direction as viewed corresponds to the "lengthwise direction" of the absorbent article, and the up-down direction as viewed corresponds to the widthwise direction of the absorbent article. Also, as seen from FIG. 7, the AB diffusion length was discernible from above the top sheet.

TABLE 5

| Absorbent article No. | 1 | 2 | 3 |
|---|---|---|---|
| TS diffusion length (lengthwise direction) | 38 mm | 34 mm | 27 mm |
| TS diffusion length (lengthwise direction) | 33 mm | 41 mm | 20 mm |
| AB diffusion length (widthwise direction) | 52 mm | 58 mm | 33 mm |
| AB diffusion length (widthwise direction) | 52 mm | 52 mm | 30 mm |

REFERENCE SIGNS LIST

1 Sanitary napkin (absorbent article)
2 Top sheet
3 Absorbent body
3a Dense section
3b Sparse section
4 side flap
5 side sheet
6 Embossed section
6' Embossed section
7 Blood slipping agent-containing region
8 Back sheet
9 Pressure bonded section
10 Recess
11 Blood slipping agent or blood slipping agent-containing composition

The invention claimed is:

1. An absorbent article having a liquid-permeable top sheet, a liquid-impermeable back sheet and an absorbent body between the top sheet and the back sheet,
wherein the absorbent body is subjected to embossing from a surface facing the back sheet of the absorbent body, a plurality of recesses are formed on the surface facing the back sheet and a dense/sparse structure is formed across an in-plane direction of the absorbent body, while the absorbent body is embossed together with the top sheet from a surface facing the top sheet of the absorbent body, the top sheet and the absorbent body are integrally compressed at a center section in a widthwise direction in an excretory opening contact region on the surface facing the top sheet, forming a plurality of pressure bonded sections where the entirety of the top sheet in a thickness direction introverts into the absorbent body, and the absorbent body and the top sheet are contacted at least in the excretory opening contact region on the surface facing the top sheet,
the pressure bonded sections extend in a lengthwise direction of the absorbent article and the pressure bonded sections are formed in a discontinuous manner at prescribed spacings in the lengthwise direction of the absorbent article and are formed in rows at prescribed spacings in a widthwise direction of the absorbent article, the recesses are formed on the surface facing the back sheet of the absorbent body below the pressure bonded sections, the excretory opening contact region of the top sheet and the pressure bonded sections each contains a blood slipping agent with a kinematic viscosity of 0.01 to 80 mm$^2$/s at 40° C., a water holding percentage of 0.01 to 4.0 mass % and a weight-average molecular weight of less than 1,000, and the amount of blood slipping agent in the pressure bonded sections is greater than the amount of blood slipping agent in the excretory opening contact region.

2. The absorbent article according to claim 1, wherein an embossed section is provided surrounding the excretory opening contact region, and the embossed section contains the blood slipping agent.

3. The absorbent article according to claim 1, wherein the top sheet has a plurality of projections on a skin side surface of the top sheet, and a clothing side surface of the top sheet is flatter than the skin side surface of the top sheet.

4. The absorbent article according to claim 3, wherein the top sheet has a gradually densifying structure from the skin side surface of the top sheet toward the clothing side surface of the top sheet.

5. The absorbent article according to claim 1, wherein total ratio of an area of the recesses with respect to the surface facing the back sheet of the absorbent body is higher than total ratio of an area of the pressure bonded sections with respect to the surface facing the top sheet of the absorbent body.

6. The absorbent article according to claim 1, wherein the recesses formed on the surface facing the back sheet of the absorbent body are dotted recesses.

7. The absorbent article according to claim 1, wherein in the lengthwise direction and/or the widthwise direction, a pitch between the pressure bonded sections formed on the surface facing the top sheet is greater than a pitch between the recesses formed on the surface facing the back sheet of the absorbent body.

8. The absorbent article according to claim 1, wherein total ratio of an area of the recesses with respect to the surface facing the back sheet of the absorbent body is 1 and 50%, a pitch between the recesses in the lengthwise direction is 3 to 10 mm, and a pitch in the widthwise direction is 3 to 10 mm.

9. The absorbent article according to claim 1, wherein total ratio of an area of the pressure bonded sections with respect to the surface facing the top sheet of the absorbent body is 0.01 and 2.0%, an area of each of the pressure bonded sections is 1 to 20 mm$^2$, a pitch between the pressure bonded sections in the lengthwise direction is 5 to 50 mm, and a pitch in the widthwise direction is 5 to 30 mm.

10. The absorbent article according to claim 1, wherein the blood slipping agent has an IOB of 0.00 to 0.60.

11. The absorbent article according to claim 1, wherein the blood slipping agent is selected from the group consisting of following items (i) to (iii), and any combination thereof:
(i) a hydrocarbon;
(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

12. The absorbent article according to claim 1, wherein the blood slipping agent is selected from the group consisting of following items (i') to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OOCO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when two or more same or different bonds are inserted in the compound of (ii') or (iii'), the bonds are not adjacent.

13. The absorbent article according to claim 1, wherein the blood slipping agent is selected from the group consisting of following items (A) to (F), as well as any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

14. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

* * * * *